United States Patent
Hernández Neuta et al.

(10) Patent No.: US 12,360,105 B2
(45) Date of Patent: Jul. 15, 2025

(54) METHODS AND COMPOSITIONS FOR SYNCHRONIZING REACTIONS IN SITU

(71) Applicant: 10x Genomics, Inc., Pleasanton, CA (US)

(72) Inventors: Jorge Iván Hernández Neuta, Stockholm (SE); Malte Kühnemund, Stockholm (SE); Patrick J. Marks, San Francisco, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 376 days.

(21) Appl. No.: 17/877,673

(22) Filed: Jul. 29, 2022

(65) Prior Publication Data

US 2023/0041485 A1 Feb. 9, 2023

Related U.S. Application Data

(60) Provisional application No. 63/227,830, filed on Jul. 30, 2021.

(51) Int. Cl.
   *C12Q 1/6813* (2018.01)
   *C12Q 1/6876* (2018.01)
   *G01N 33/53* (2006.01)

(52) U.S. Cl.
   CPC ....... *G01N 33/5308* (2013.01); *C12Q 1/6813* (2013.01); *C12Q 1/6876* (2013.01)

(58) Field of Classification Search
   CPC ............ C12Q 1/6841; C12Q 2525/307; C12Q 2531/125; C12Q 2527/127; C12Q 2543/101
   See application file for complete search history.

(56) References Cited

U.S. PATENT DOCUMENTS

| | | |
|---|---|---|
| 4,318,846 A | 3/1982 | Khanna et al. |
| 4,683,195 A | 7/1987 | Mullis et al. |
| 4,683,202 A | 7/1987 | Mullis |
| 4,757,141 A | 7/1988 | Fung et al. |
| 4,800,159 A | 1/1989 | Mullis et al. |
| 4,849,336 A | 7/1989 | Miyoshi et al. |
| 4,965,188 A | 10/1990 | Mullis et al. |
| 5,066,580 A | 11/1991 | Lee |
| 5,091,519 A | 2/1992 | Cruickshank |
| 5,151,507 A | 9/1992 | Hobbs et al. |
| 5,188,934 A | 2/1993 | Menchen |
| 5,198,537 A | 3/1993 | Huber et al. |
| 5,344,757 A | 9/1994 | Holtke et al. |
| 5,354,657 A | 10/1994 | Boehringer et al. |
| 5,366,860 A | 11/1994 | Bergot et al. |
| 5,409,811 A | 4/1995 | Tabor et al. |
| 5,512,462 A | 4/1996 | Cheng |
| 5,599,675 A | 2/1997 | Brenner |
| 5,635,352 A | 6/1997 | Urdea et al. |
| 5,688,648 A | 11/1997 | Mathies |
| 5,695,940 A | 12/1997 | Drmanac et al. |
| 5,702,888 A | 12/1997 | Holtke et al. |
| 5,750,341 A | 5/1998 | Macevicz |
| 5,800,996 A | 9/1998 | Lee et al. |
| 5,847,162 A | 12/1998 | Lee et al. |
| 5,990,479 A | 11/1999 | Weiss et al. |
| 6,054,274 A | 4/2000 | Sampson et al. |
| 6,172,218 B1 | 1/2001 | Brenner |
| 6,207,392 B1 | 3/2001 | Weiss et al. |
| 6,251,303 B1 | 6/2001 | Bawendi et al. |
| 6,265,552 B1 | 7/2001 | Schatz |
| 6,291,187 B1 | 9/2001 | Kingsmore et al. |
| 6,306,597 B1 | 10/2001 | Macevicz |
| 6,319,426 B1 | 11/2001 | Bawendi et al. |
| 6,322,901 B1 | 11/2001 | Bawendi et al. |
| 6,323,009 B1 | 11/2001 | Lasken et al. |
| 6,344,329 B1 | 2/2002 | Lizardi et al. |
| 6,368,801 B1 | 4/2002 | Faruqi |
| 6,391,937 B1 | 5/2002 | Beuhler et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |

(Continued)

FOREIGN PATENT DOCUMENTS

| | | |
|---|---|---|
| WO | WO 1991/017160 | 11/1991 |
| WO | WO 2014/076209 | 5/2014 |

(Continued)

OTHER PUBLICATIONS

Chen et al., "Efficient in situ barcode sequencing using padlock probe-based BaristaSeq," Nucleic Acids Res. (2018) 46(4): e22.
Sun et al., "Integrating barcoded neuroanatomy with spatial transcriptional profiling enables identification of gene correlates of projections," Nat Neurosci. (2021) 24(6):873-885.
Archer et al., "Selective and flexible depletion of problematic sequences from RNA-seq libraries at the cDNA stage," BMC Genomics. (2014) 15(1):401.
Baner et al., "Signal amplification of padlock probes by rolling circle replication," Nucleic Acids Res. (1998) 26(22):5073-5078.
Bibikova et al., "Quantitative gene expression profiling in formalin-fixed, paraffin-embedded tissues using universal bead arrays," Am J Pathol. Nov. 2004; 165(5):1799-807.
Bolognesi et al., "Multiplex Staining by Sequential Immunostaining and Antibody Removal on Routine Tissue Sections," J. Histochem. Cytochem. (2017); 65(8): 431-444.

(Continued)

*Primary Examiner* — Young J Kim
(74) *Attorney, Agent, or Firm* — MORRISON & FOERSTER LLP

(57) ABSTRACT

The present disclosure in some aspects relates to methods and compositions for accurately detecting and quantifying multiple analytes present in a biological sample. In some aspects, the methods and compositions provided herein address issues associated with the heterogeneity of analyte abundance (e.g., gene expression levels) and variations among reactions at different locations of a sample (e.g., amplification reaction starting earlier at one location than another location). In some aspects, a method disclosed herein provides a tighter distribution of signal spot size and intensity in a sample, as compared to methods that result in a wide and heterogeneous size and intensity distribution of signal spots.

20 Claims, 8 Drawing Sheets

(56) References Cited

U.S. PATENT DOCUMENTS

| | | |
|---|---|---|
| 6,534,266 B1 | 3/2003 | Singer |
| 6,576,291 B2 | 6/2003 | Bawendi et al. |
| 6,828,109 B2 | 12/2004 | Kaplan et al. |
| 6,969,488 B2 | 11/2005 | Bridgham et al. |
| 7,057,026 B2 | 6/2006 | Barnes et al. |
| 7,255,994 B2 | 8/2007 | Lao |
| 7,264,929 B2 | 9/2007 | Rothberg et al. |
| 7,345,159 B2 | 3/2008 | Ju et al. |
| 7,473,767 B2 | 1/2009 | Dimitrov |
| 7,534,991 B2 | 5/2009 | Miller et al. |
| 7,544,794 B1 | 6/2009 | Benner |
| 7,555,155 B2 | 6/2009 | Levenson et al. |
| 7,566,537 B2 | 7/2009 | Balasubramanian et al. |
| 7,632,641 B2 | 12/2009 | Dirks et al. |
| 7,655,898 B2 | 2/2010 | Miller |
| 7,721,721 B1 | 5/2010 | Kronengold et al. |
| 7,893,227 B2 | 2/2011 | Wu et al. |
| 7,910,304 B2 | 3/2011 | Drmanac |
| 7,914,987 B2 | 3/2011 | Fredriksson et al. |
| 7,941,279 B2 | 5/2011 | Hwang et al. |
| 7,989,166 B2 | 8/2011 | Koch et al. |
| 8,062,654 B2 | 11/2011 | Nelson et al. |
| 8,124,751 B2 | 2/2012 | Pierce et al. |
| 8,133,672 B2 | 3/2012 | Bjornson et al. |
| 8,199,999 B2 | 6/2012 | Hoyt et al. |
| 8,257,954 B2 | 9/2012 | Clark et al. |
| 8,268,554 B2 | 9/2012 | Schallmeiner |
| 8,330,087 B2 | 12/2012 | Domenicali |
| 8,343,746 B2 | 1/2013 | Rank et al. |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,580,504 B2 | 11/2013 | Fredriksson et al. |
| 8,632,975 B2 | 1/2014 | Vander Horn et al. |
| 8,658,361 B2 | 2/2014 | Wu et al. |
| 8,658,365 B2 | 2/2014 | Bjornson et al. |
| 8,771,950 B2 | 7/2014 | Church et al. |
| 8,921,086 B2 | 12/2014 | Hanzel et al. |
| 8,986,926 B2 | 3/2015 | Ferree et al. |
| 9,201,063 B2 | 12/2015 | Sood et al. |
| 9,217,178 B2 | 12/2015 | Fedurco et al. |
| 9,273,349 B2 | 3/2016 | Nguyen et al. |
| 9,279,155 B2 | 3/2016 | Bjornson et al. |
| 9,371,563 B2 | 6/2016 | Geiss et al. |
| 9,371,598 B2 | 6/2016 | Chee |
| 9,376,717 B2 | 6/2016 | Gao et al. |
| 9,512,422 B2 | 12/2016 | Barnard et al. |
| 9,541,504 B2 | 1/2017 | Hoyt |
| 9,551,032 B2 | 1/2017 | Landegren et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,889,422 B2 | 2/2018 | Smith et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,174,281 B1 | 11/2021 | Graham et al. |
| 11,287,422 B2 | 3/2022 | Previte et al. |
| 11,434,525 B2 | 9/2022 | Glezer |
| 11,459,603 B2 | 10/2022 | Tyagi et al. |
| 11,499,185 B2 | 11/2022 | Vijayan et al. |
| 11,643,679 B2 | 5/2023 | Glezer et al. |
| 11,999,999 B2 | 6/2024 | Ju et al. |
| 2002/0045045 A1 | 4/2002 | Adams et al. |
| 2003/0017264 A1 | 1/2003 | Treadway et al. |
| 2005/0100900 A1 | 5/2005 | Kawashima et al. |
| 2006/0188901 A1 | 8/2006 | Barnes et al. |
| 2006/0234261 A1 | 10/2006 | Pierce et al. |
| 2006/0240439 A1 | 10/2006 | Smith et al. |
| 2006/0281109 A1 | 12/2006 | Barr et al. |
| 2007/0166705 A1 | 7/2007 | Milton et al. |
| 2009/0118128 A1 | 5/2009 | Liu et al. |
| 2010/0055733 A1 | 3/2010 | Lutolf et al. |
| 2011/0059865 A1 | 3/2011 | Smith et al. |
| 2011/0223585 A1 | 9/2011 | Gullberg et al. |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2013/0288249 A1 | 10/2013 | Gullbert |
| 2013/0323729 A1 | 12/2013 | Landegren et al. |
| 2014/0194311 A1 | 6/2014 | Gullberg et al. |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0219465 A1 | 8/2017 | Desseroth et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0164308 A1* | 6/2018 | Walter ................ C12Q 1/6806 |
| 2018/0208967 A1 | 7/2018 | Larman et al. |
| 2018/0237864 A1 | 8/2018 | Imler et al. |
| 2018/0251833 A1 | 9/2018 | Daugharthy et al. |
| 2018/0320226 A1 | 11/2018 | Church et al. |
| 2019/0017106 A1 | 1/2019 | Frisen et al. |
| 2019/0032121 A1 | 1/2019 | Daugharthy et al. |
| 2019/0032128 A1 | 1/2019 | Chen et al. |
| 2019/0055594 A1 | 2/2019 | Samusik et al. |
| 2019/0106733 A1 | 4/2019 | Kishi et al. |
| 2019/0112599 A1 | 4/2019 | Church et al. |
| 2019/0119735 A1 | 4/2019 | Deisseroth et al. |
| 2019/0144940 A1 | 5/2019 | Landegren et al. |
| 2019/0155835 A1 | 5/2019 | Daugharthy et al. |
| 2019/0161796 A1 | 5/2019 | Hauling et al. |

(56) References Cited

U.S. PATENT DOCUMENTS

| | | |
|---|---|---|
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2019/0367969 A1 | 12/2019 | Belhocine |
| 2019/0376956 A1 | 12/2019 | Bobrow et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0248258 A1 | 8/2020 | Arslan et al. |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2020/0399689 A1 | 12/2020 | Luo et al. |
| 2021/0017587 A1 | 1/2021 | Cai et al. |
| 2021/0047669 A1 | 2/2021 | Nguyen |
| 2021/0115504 A1 | 4/2021 | Cai et al. |
| 2021/0164039 A1 | 6/2021 | Wang et al. |
| 2021/0198723 A1 | 7/2021 | Kuhnemund et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340618 A1 | 11/2021 | Kuhnemund et al. |
| 2021/0340621 A1 | 11/2021 | Daugharthy et al. |
| 2021/0388423 A1 | 12/2021 | Bava et al. |
| 2021/0388424 A1 | 12/2021 | Bava |
| 2021/0403993 A1 | 12/2021 | Pugliese et al. |
| 2022/0010358 A1 | 1/2022 | Kuhnemund et al. |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0186310 A1 | 6/2022 | Arslan et al. |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava |
| 2022/0282319 A1 | 9/2022 | Verheyen |
| 2022/0372570 A1 | 11/2022 | Costa |
| 2022/0380838 A1 | 12/2022 | Kuhnemund et al. |
| 2022/0403353 A1 | 12/2022 | Ambroso et al. |
| 2022/0403458 A1 | 12/2022 | Bava |
| 2023/0002808 A1 | 1/2023 | Mignardi |
| 2023/0012607 A1 | 1/2023 | Kuhnemund et al. |
| 2023/0013775 A1 | 1/2023 | Chen et al. |
| 2023/0015226 A1 | 1/2023 | Chen et al. |
| 2023/0026886 A1 | 1/2023 | Chen |
| 2023/0031305 A1 | 2/2023 | Hernandez Neuta et al. |
| 2023/0031996 A1 | 2/2023 | Hernandez Neuta et al. |
| 2023/0035685 A1 | 2/2023 | Hernandez Neuta et al. |
| 2023/0037182 A1 | 2/2023 | Bava et al. |
| 2023/0039148 A1 | 2/2023 | Verheyen |
| 2023/0044650 A1 | 2/2023 | Dockter |
| 2023/0057571 A1 | 2/2023 | Costa et al. |
| 2023/0061542 A1 | 3/2023 | Kuhnemund |
| 2023/0084407 A1 | 3/2023 | Hernandez Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0242974 A1 | 8/2023 | Costa et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Schnall-Levin |
| 2023/0323430 A1 | 10/2023 | Shastry |
| 2023/0323437 A1 | 10/2023 | Chen et al. |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Bava |
| 2024/0026427 A1 | 1/2024 | Kuhnemund et al. |
| 2024/0026439 A1 | 1/2024 | Sasaki |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen et al. |
| 2024/0060119 A1 | 2/2024 | Bava |
| 2024/0084373 A1 | 3/2024 | Shastry |
| 2024/0084378 A1 | 3/2024 | Marks et al. |
| 2024/0101978 A1 | 3/2024 | Boghospor et al. |
| 2024/0132938 A1 | 4/2024 | Kuhnemund |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |
| 2024/0263219 A1 | 8/2024 | Kuhnemund |
| 2024/0263220 A1 | 8/2024 | Olofsson |
| 2024/0264155 A1 | 8/2024 | Costa |

FOREIGN PATENT DOCUMENTS

| | | |
|---|---|---|
| WO | WO 2014/163886 | 10/2014 |
| WO | WO 2016/016452 | 2/2016 |
| WO | WO 2016/034849 A1 | 3/2016 |
| WO | WO 2017/079406 | 5/2017 |
| WO | WO 2017/143155 | 8/2017 |
| WO | WO 2018/026873 | 2/2018 |
| WO | WO 2018/033528 | 2/2018 |
| WO | WO 2019/199579 | 10/2019 |
| WO | WO 2019/236841 | 12/2019 |
| WO | WO 2020/076976 | 4/2020 |
| WO | WO 2020/076979 | 4/2020 |
| WO | 2020/101795 | 5/2020 |
| WO | WO 2020/096687 | 5/2020 |
| WO | WO 2020/099640 | 5/2020 |
| WO | WO 2020/102094 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/163397 | 8/2020 |
| WO | WO 2020/240025 | 12/2020 |
| WO | WO 2020/254519 | 12/2020 |
| WO | WO 2021/067475 | 4/2021 |
| WO | WO 2021/123282 | 6/2021 |
| WO | WO 2021/123286 | 6/2021 |
| WO | WO 2021/138676 | 7/2021 |
| WO | WO 2021/155063 | 8/2021 |
| WO | WO 2021/168326 | 8/2021 |
| WO | WO 2023/009842 | 2/2023 |
| WO | WO 2023/108139 | 6/2023 |
| WO | WO 2023/141476 | 7/2023 |
| WO | WO 2023/172915 | 9/2023 |

(56) References Cited

FOREIGN PATENT DOCUMENTS

| WO | WO 2023/192302 | 10/2023 |
|----|----------------|---------|
| WO | WO 2024/148300 | 7/2024  |

OTHER PUBLICATIONS

Capodieci et al., "Gene expression profiling in single cells within tissue," Nat Methods. (2005) 2(9): 663-5.

Chemeris et al., "Real-time hybridization chain reaction," Dokl Biochem Biophys. (2008) 419: 53-55.

Chen et al., "Nanoscale imaging of RNA with expansion microscopy," Nat Methods. (2016) 13:679-684.

Chen et al., "RNA imaging. Spatially resolved, highly multiplexed RNA profiling in single cells," Science. (2015) 348(6233): aaa6090. 16 pgs.

Chen et al., "Expansion Microscopy," Science (2015) 347(6221):543-548.

Choi et al., "Programmable in situ amplification for multiplexed imaging of mRNA expression," Nat Biotechnol. (2010) 28(11): 1208-1212.

Conze et al., "Single molecule analysis of combinatorial splicing," Nucleic Acids Res. (2010) 38(16): e163.

Dean et al., "Rapid Amplification of Plasmid and Phage DNA Using Phi29 DNA Polymerase and Multiply-Primed Rolling Circle Amplification," Genome Research (2001) 11:1095-1099.

Dirks et al., "Triggered amplification by hybridization chain reaction," Proc Natl Acad Sci USA. (2004) 101(43): 15275-15278.

Eng et al., "Transcriptome-scale super-resolved imaging in tissues by RNA seqFISH," Nature. (2019) 568(7751): 235-239.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Faruqi et al., "High-throughput genotyping of single nucleotide polymorphisms with rolling circle amplification," BMC Genomics. (2001) 2:4.

Femino et al., "Visualization of single RNA transcripts in situ," Science. (1998) 280(5363): 585-90.

Forcucci et al., "All-plastic miniature fluorescence microscope for point-of-care readout of bead-based bioassays," J Biomed Opt. (2015) 20(10): 105010.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging in Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Gunderson et al. "Decoding randomly ordered DNA arrays." Genome research 14.5 (2004): 870-877.

Gyllborg et al., "Hybridization-based in situ sequencing (HybISS) for spatially resolved transcriptomics in human and mouse brain tissue," Nucleic Acids Res. (2020) 48(19): e112.

Han et al., "Quantum-dot-tagged microbeads for multiplexed optical coding of biomolecules," Nat Biotechnol. (2001) 19(7): 631-5.

Henegariu et al., "Custom fluorescent-nucleotide synthesis as an alternative method for nucleic acid labeling," Nature Biotechnol. (2000) 18:345.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Jamur et al., "Permeabilization of cell membranes," Method Mol. Biol. (2010) 588: 63-66 (abstract only).

Korlach et al. "Selective aluminum passivation for targeted immobilization of single DNA polymerase molecules in zero-mode waveguide nanostructures." *Proceedings of the National Academy of Sciences* 105.4 (2008): 1176-1181.

Krzywkowski et al., "Fidelity of RNA templated end-joining by chlorella virus DNA ligase and a novel iLock assay with improved direct RNA detection accuracy," Nucleic Acids Res. (2017) 45(18): e161.

Lagunavicius et al., "Novel application of Phi29 DNA polymerase: RNA detection and analysis in vitro and in situ by target RNA-primed RCA," RNA. (2009) 15(5):765-71.

Lakowicz et al., "Silver particles enhance emission of fluorescent DNA oligomers," Bio Techniques (2003) 34(1); 62-66.

Larsson et al. "In situ detection and genotyping of individual mRNA molecules," Nat Methods. (2010) 7(5):395-397.

Lee et al. "Highly Multiplexed Subcellular RNA Sequencing In Situ", Science (2014) 343(6177):1360-1363.

Levene et al. "Zero-mode waveguides for single-molecule analysis at high concentrations." science 299.5607 (2003): 682-686.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Lin et al., "Highly multiplexed imaging of single cells using a high-throughput cyclic immunofluorescence method," Nat Commun. (2015) 6:8390.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lizardi et al., "Mutation detection and single-molecule counting using isothermal rolling-circle amplification," Nat Genet. (1998) 19(3): 225-232.

Lundquist et al. "Parallel confocal detection of single molecules in real time." Optics letters 33.9 (2008): 1026-1028.

Lyamichev et al., "Comparison of the 5' nuclease activities of taq DNA polymerase and its isolated nuclease domain," Proc Natl Acad Sci USA. (1999) 96(11): 6143-6148.

Ma et al., "RNA template-dependent 5' nuclease activity of Thermus aquaticus and Thermus thermophilus DNA polymerases," J Biol Chem. (2000) 275(32): 24693-700.

Maierhorfer et al., "Multicolor deconvolution microscopy of thick biological specimens," Am J Pathol. (2003) 162(2): 373-9.

McGinn et al., "New technologies for DNA analysis—a review of the READNA Project," N Biotechnol. (2016) 33(3): 311-30. doi: 10.1016/j.nbt.2015.10.003.

Meade et al. "Multiplexed DNA detection using spectrally encoded porous SiO2 photonic crystal particles," Anal Chem. (2009) 81(7): 2618-25.

Mitra et al., "Fluorescent in situ sequencing on polymerase colonies," Anal. Biochem. (2003) 320, 55-65.

Moffitt et al., "RNA Imaging with Multiplexed Error-Robust Fluorescence In Situ Hybridization (MERFISH)," Methods in Enzymology, (2016) 572; 1-49.

Mohsen et al., "The Discovery of Rolling Circle Amplification and Rolling Circle Transcription," Acc Chem Res. (2016) 49(11): 2540-2550.

Nallur et al., "Signal amplification by rolling circle amplification on DNA microarrays," Nucleic Acids Res. (2001) 29(23): e118.

Niu et al., "Fluorescence detection for DNA using hybridization chain reaction with enzyme-amplification," Chem Commun (Camb). (2010) 46(18): 3089-91.

Payne et al. "In situ genome sequencing resolves DNA sequence and structure in intact biological samples," Science. (2021) 371(6532): eaay3446. doi: 10.1126/science.aay3446. Epub Dec. 31, 2020.

Pirici et al., "Antibody elution method for multiple immunohistochemistry on primary antibodies raised in the same species and of the same subtype," J Histochem Cytochem. (2009) 57(6); 567-75.

(56) References Cited

OTHER PUBLICATIONS

Raj et al., "Imaging individual mRNA molecules using multiple singly labeled probes," Nat Methods. (2008) 5(10): 877-879.
Rajeswari et al., "Multiple pathogen biomarker detection using an encoded bead array in droplet PCR," J Microbiol Methods. (2017) 139: 22-28.
Rouhanifard et al. "ClampFISH detects individual nucleic acid molecules using click chemistry-based amplification," Nat Biotechnol. (2018) 17 pages. doi: 10.1038/nbt.4286.
Schweitzer et al. "Immunoassays with rolling circle DNA amplification: A versatile platform for ultrasensitive antigen detection," Proc. Natl Acad. Sci. USA (2000) 97:10113-119.
Schweitzer et al., "Multiplexed protein profiling on microarrays by rolling-circle amplification," Nature Biotech. (2002) 20:359-365.
Shendure et al., "Accurate multiplex polony sequencing of an evolved bacterial genome," Science (2005) 309(5741); 1728-1732.
Song et al., "Hybridization chain reaction-based aptameric system for the highly selective and sensitive detection of protein," Analyst. (2012) 137(6):1396-1401.
Sun et al., "Composite organic-inorganic nanoparticles as Raman labels for tissue analysis," Nano Lett. (2007) 7(2): 351-6.
Takei et al., (Feb. 2021, e-pub Jan. 27, 2021). "Integrated Spatial Genomics Reveals Global Architecture of Single Nuclei," Nature 590(7845):344-350, 53 pages. doi: 10.1038/s41586-020-03126-2.
Vandernoot et al., "cDNA normalization by hydroxyapatite chromatography to enrich transcriptome diversity in RNA-seq applications," Biotechniques, (2012) 53(6) 373-80.
Vashishtha et al., "Different Divalent Cations Alter the Kinetics and Fidelity of DNA Polymerases," J Biol Chem. (2016) 291(40):20869-20875.
Wählby et al., "Sequential immunofluorescence staining and image analysis for detection of large numbers of antigens in individual cell nuclei," Cytometry. (2002) 47(1):32-41.
Wang et al., "Three-dimensional intact-tissue sequencing of single-cell transcriptional states," Science. (2018) 361(6400): eaat5691.
Weibrecht et al., "Simultaneous visualization of both signaling cascade activity and end-point gene expression in single cells," PLoS One. (2011) 6(5): e20148.
Wetmur, "DNA Probes: Applications of the Principles of Nucleic Acid Hybridization," Critical Reviews in Biochemistry and Molecular Biology, (1991) 26(91); 227-259.
Wilson et al., "Encoded microcarriers for high-throughput multiplexed detection," Angew Chem Int Ed Engl. (2006) 18;45(37): 6104-17.
Wu et al., "RollFISH Achieves Robust Quantification of Single-Molecule RNA Biomarkers in Paraffin-Embedded Tumor Tissue Samples," Commun Biol. (2018) 1:(209):1-8. doi: 10.1038/s42003-018-0218-0.
Xia et al. "Multiplexed detection of RNA using MERFISH and branched DNA amplification." Scientific reports 9.1 (2019): 1-13.
Zhao et al., "Advances of multiplex and high throughput biomolecular detection technologies based on encoding microparticles," Sci China Chem. (2011) 54(8):1185.
Eid et al., "Real-time DNA sequencing from single polymerase molecules," Science. (2009) 323(5910):133-8.
Lieberman et al., "Processive replication of single DNA molecules in a nanopore catalyzed by phi29 DNA polymerase," J Am Chem Soc. (2010) 132(50):17961-72.
Clausson et al., "Compaction of rolling circle amplification products increases signal integrity and signal-to-noise ratio," Sci Rep. (2015) 5:12317.

\* cited by examiner

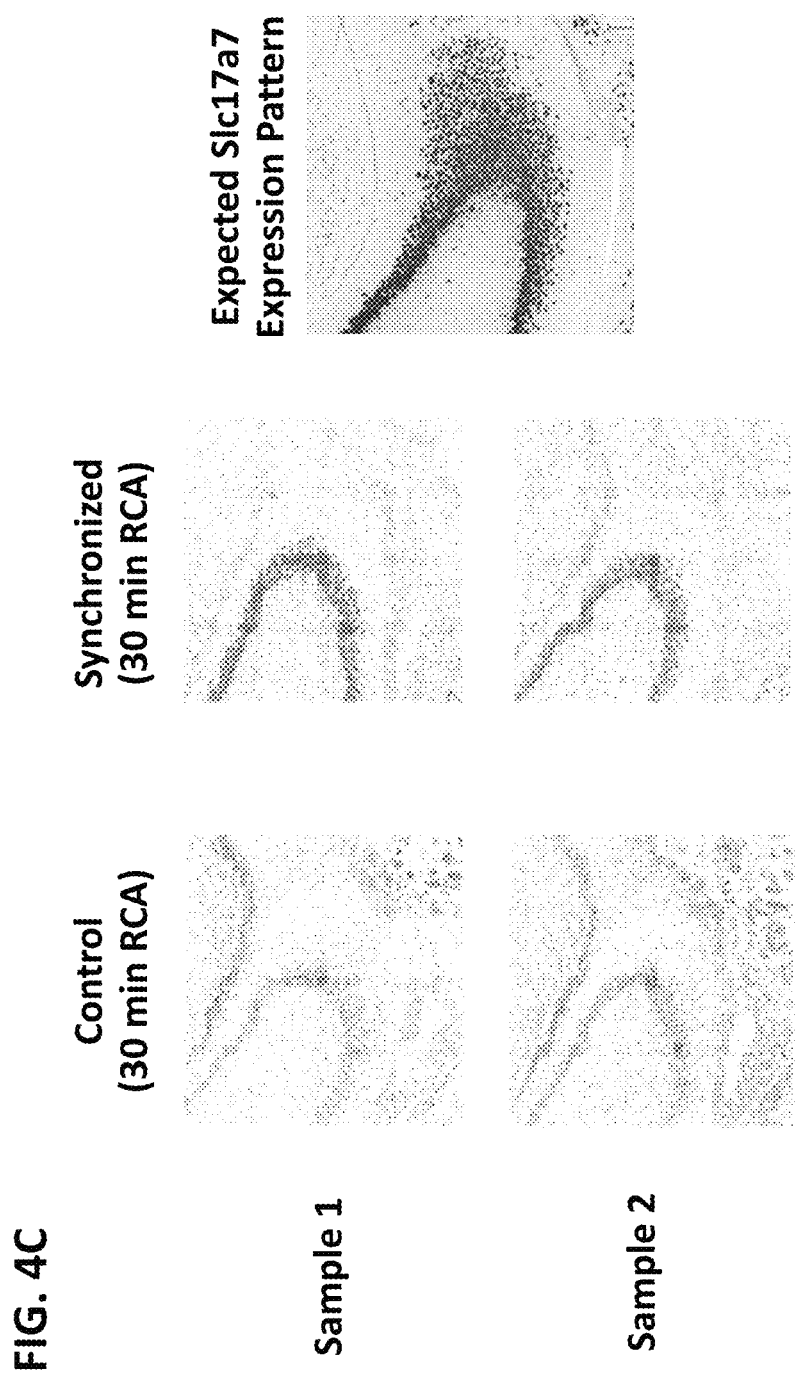

METHODS AND COMPOSITIONS FOR SYNCHRONIZING REACTIONS IN SITU

CROSS-REFERENCE TO RELATED APPLICATIONS

This application claims priority to U.S. Provisional Patent Application No. 63/227,830 filed Jul. 30, 2021, entitled "METHOD AND COMPOSITIONS FOR SYNCHRONIZING REACTIONS IN SITU," which is herein incorporated by reference in its entirety for all purposes.

FIELD

The present disclosure generally relates to methods and compositions for in situ detection of a plurality of molecules of one or more analytes in a sample.

BACKGROUND

Genomic, transcriptomic, and proteomic profiling of cells and tissue samples using microscopic imaging can resolve multiple analytes of interest at the same time, thereby providing valuable information regarding analyte abundance and localization in situ. Thus, these in situ assays are important tools, for example, for understanding the molecular basis of cell identity and developing treatment for diseases. In multiplex assays where multiple signals are detected simultaneously, it is important that as much information as possible is collected. However, due to the heterogeneity of analyte abundance (e.g., gene expression levels) and variations among reactions at different locations of a sample, there can be a wide and heterogeneous size and intensity distribution of signal "spots" in the sample. Large signal spots may overlap with one another and/or mask adjacent smaller signal spots, rendering the smaller spots unresolvable. In addition, some analytes may be associated with bright signal spots (e.g., due to high analyte abundance and/or preferential signal amplification), while other analytes may be associated with signal spots that are too dim to be detected simultaneously (e.g., in the same field of view (FOV) during microscopy) with the bright spots. There is a need for new and improved methods for in situ assays. The present disclosure addresses these and other needs.

SUMMARY

In some embodiments, provided herein is a method for analyzing a biological sample, comprising contacting the biological sample with a first reaction mixture, wherein the biological sample comprises a circular nucleic acid comprising a hybridization region, the first reaction mixture comprises a polymerase, the circular nucleic acid or the polymerase is prebound to a polynucleotide comprising a sequence complementary to the hybridization region, and the polymerase activity of the polymerase is inhibited. In some embodiments, the method further comprises contacting the biological sample with a second reaction mixture to allow the polymerase to extend the polynucleotide hybridized to the hybridization region using the circular nucleic acid as a template. In any of the preceding embodiments, a rolling circle amplification product of the circular nucleic acid can be generated in the biological sample, for instance, for in situ analysis of the circular nucleic acid and/or one or more analytes of interest associated therewith.

In any of the preceding embodiments, the first reaction mixture can stabilize the polymerase and/or inhibit an activity of the polymerase, such as a polymerase activity and/or a nuclease activity. In any of the preceding embodiments, the first reaction mixture can comprise one or more deoxynucleoside triphosphates (dNTPs) and/or nucleoside triphosphates (NTPs). In any of the preceding embodiments, the first reaction mixture can comprise dATP, dTTP, dCTP, and/or dGTP. Alternatively, in any of the preceding embodiments, the first reaction mixture can be substantially free of dNTPs and/or NTPs. In any of the preceding embodiments, the first reaction mixture can comprise a di-cation that is not a cofactor of the polymerase. In some embodiments, the di-cation is $Ca^{2+}$. In any of the preceding embodiments, the di-cation can stabilize the polymerase. In any of the preceding embodiments, the di-cation can stabilize a preformed complex comprising the polymerase and the polynucleotide. In any of the preceding embodiments, the first reaction mixture can be substantially free of a cofactor of the polymerase. In any of the preceding embodiments, the first reaction mixture can be substantially free of $Mg^{2+}$, $Co^{2+}$, and/or $Mn^{2+}$. In any of the preceding embodiments, the first reaction mixture can comprise a chelating agent. For instance, the chelating agent can chelate a di-cation such as $Mg^{2+}$ from one or more prior reactions. As such, the chelating agent can chelate residual amounts of the di-cation in the biological sample, such as a tissue slice which has been contacted with a reaction mixture containing the di-cation (e.g., a ligation reaction mixture to circularize a padlock probe to form the circular nucleic acid). In any of the preceding embodiments, the first reaction mixture can comprise EDTA, EGTA, BAPTA, DTPA, or a combination thereof. In any of the preceding embodiments, the first reaction mixture can inhibit the polymerase activity and/or an exonuclease activity of the polymerase. In any of the preceding embodiments, the 3'→5' exonuclease activity and/or the 5'→3' exonuclease activity of the polymerase can be inhibited in the first reaction mixture.

In any of the preceding embodiments, the polynucleotide can comprise a 3' protective group and/or a 5' protective group. In any of the preceding embodiments, the polynucleotide can comprise a free 3' hydroxyl that is available for extension by a polymerase. In any of the preceding embodiments, the polynucleotide can be 3' thiophosphate-protected, thereby protecting the polynucleotide from 3'→5' exonuclease degradation by the polymerase while allowing priming by the polymerase.

In any of the preceding embodiments, the polynucleotide can be a primer, and the primer is prebound to the polymerase in the first reaction mixture prior to contacting the biological sample. In any of the preceding embodiments, the method can comprise removing one or more complexes comprising the polymerase and the primer that are not bound to the circular nucleic acid from the biological sample prior to contacting the biological sample with the second reaction mixture. Thus, in some embodiments, provided herein is a method for analyzing a biological sample, comprising: contacting the biological sample with a first reaction mixture, wherein the biological sample comprises a circular nucleic acid comprising a primer hybridization region, the first reaction mixture comprises a polymerase, the circular nucleic acid or the polymerase is prebound to a primer comprising a sequence complementary to the primer hybridization region, and the polymerase activity of the polymerase is inhibited; and contacting the biological sample with a second reaction mixture to allow the polymerase to extend the primer hybridized to the primer hybridization region using the circular nucleic acid as a template, wherein a rolling circle amplification product of the circular nucleic acid is generated in the biological sample.

In any of the preceding embodiments, the polynucleotide can be prebound to the circular nucleic acid in the biological sample prior to contacting the first reaction mixture. In any of the preceding embodiments, the polynucleotide can be a primer, and the primer is prebound to the circular nucleic acid in the biological sample prior to contacting the first reaction mixture. In any of the preceding embodiments, the hybridization region in the circular nucleic acid can be a primer hybridization region that hybridizes to the primer, and the circular nucleic acid can further comprise a target hybridization region that hybridizes to a target nucleic acid. In any of the preceding embodiments, the target nucleic acid can be a DNA or RNA molecule in the biological sample, a product of the DNA or RNA molecule, a probe that directly or indirectly binds to the DNA or RNA molecule, or a product of the probe. In any of the preceding embodiments, the target nucleic acid can comprise a genomic DNA sequence, an RNA sequence, and/or a cDNA sequence.

In any of the preceding embodiments, the polynucleotide can be a target nucleic acid. In any of the preceding embodiments, the target nucleic acid can be prebound to the circular nucleic acid in the biological sample prior to contacting the first reaction mixture. In any of the preceding embodiments, the target nucleic acid can comprise a genomic DNA sequence, an RNA sequence, and/or a cDNA sequence. In any of the preceding embodiments, the target nucleic acid can comprise a free 3' end for priming the rolling circle amplification. In any of the preceding embodiments, the target nucleic acid can be processed (e.g., by an enzyme having 3'→5' exonuclease activity such as Phi29) to provide a free 3' end for priming the rolling circle amplification. In any of the preceding embodiments, the method can further comprise removing one or more molecules of the polymerase that are not bound to the circular nucleic acid from the biological sample prior to contacting the biological sample with the second reaction mixture.

In any of the preceding embodiments, the polymerase may not be attached to a nanopore, a nanopore membrane or an insulating support thereof. In any of the preceding embodiments, the polymerase can be diffusible in the first reaction mixture and/or in the biological sample. In any of the preceding embodiments, a preformed complex comprising the polymerase and the polynucleotide can be diffusible in the first reaction mixture and/or in the biological sample.

In any of the preceding embodiments, the polymerase may be selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof.

In any of the preceding embodiments, the polymerase may be a Phi29 DNA polymerase or a variant or derivative thereof.

In any of the preceding embodiments, the polynucleotide can be prebound to a single-stranded DNA binding domain of the Phi29 DNA polymerase. In some embodiments, the polynucleotides is a primer prebound to a single-stranded DNA binding domain of the Phi29 DNA polymerase in the first reaction mixture. In any of the preceding embodiments, the polynucleotide bound to the Phi29 DNA polymerase can be hybridized to the hybridization region and the Phi29 DNA polymerase can be prevented from extending the polynucleotide until the biological sample is contacted with the second reaction mixture.

In any of the preceding embodiments, the method can further comprise, between the contacting with the first reaction mixture and with the second reaction mixture, a step of removing molecules of the polymerase and/or the polynucleotide that are not bound to the circular nucleic acid from the biological sample. In any of the preceding embodiments, the method can further comprise one or more stringency washes between the contacting steps.

In any of the preceding embodiments, the second reaction mixture can comprise a deoxynucleoside triphosphate (dNTP) and/or a nucleoside triphosphate (NTP). In any of the preceding embodiments, the second reaction mixture can comprise a cofactor of the polymerase. In any of the preceding embodiments, the second reaction mixture can comprise a di-cation, such as $Mg^{2+}$, $Co^{2+}$, and/or $Mn^{2+}$. In any of the preceding embodiments, the second reaction mixture can be substantially free of the polymerase and/or other polymerases. In any of the preceding embodiments, the pH of the first and second reaction mixtures can be substantially the same, e.g., about pH 8.5. In any of the preceding embodiments, the pH of the first and second reaction mixtures can be independently about 7.0, about 7.5, about 8.0, about 8.5, about 9.0, about 9.5, or about 10.0. In any of the preceding embodiments, the pH of the first and second reaction mixtures can be independently about 8.1, about 8.2, about 8.3, about 8.4, about 8.5, about 8.6, about 8.7, about 8.8, about 8.9, or about 9.0.

In any of the preceding embodiments, the polynucleotide hybridized to the hybridization region can be extended by the polymerase using the circular nucleic acid as a template, thereby generating the rolling circle amplification product. In any of the preceding embodiments, the rolling circle amplification product can be generated using a linear rolling circle amplification (RCA), a branched RCA, a dendritic RCA, or any combination thereof. In any of the preceding embodiments, the rolling circle amplification product can be generated in situ. In any of the preceding embodiments, the rolling circle amplification product can be immobilized in the biological sample. In any of the preceding embodiments, the rolling circle amplification product can be crosslinked to one or more other molecules in the biological sample. In any of the preceding embodiments, the method can comprise imaging the biological sample to detect the rolling circle amplification product. In any of the preceding embodiments, the imaging can comprise detecting a signal associated with a fluorescently labeled probe that directly or indirectly binds to the rolling circle amplification product.

In any of the preceding embodiments, a signal associated with the rolling circle amplification product can be amplified in situ in the biological sample. In any of the preceding embodiments, the signal amplification in situ can comprise rolling circle amplification (RCA) of a probe that directly or indirectly binds to the rolling circle amplification product, hybridization chain reaction (HCR) directly or indirectly on the rolling circle amplification product, linear oligonucleotide hybridization chain reaction (LO-HCR) directly or indirectly on the rolling circle amplification product, primer exchange reaction (PER) directly or indirectly on the rolling circle amplification product, assembly of branched structures directly or indirectly on the rolling circle amplification product, hybridization of a plurality of detectable probes directly or indirectly on the rolling circle amplification product, or any combination thereof.

In any of the preceding embodiments, a sequence of the rolling circle amplification product can be analyzed in situ in the biological sample. In any of the preceding embodiments, the sequence of the rolling circle amplification product can be analyzed by sequential hybridization, sequencing by hybridization, sequencing by ligation, sequencing by synthesis, sequencing by binding, or a combination thereof. In any of the preceding embodiments, the sequence of the rolling circle amplification product can comprise a barcode sequence or complement thereof.

In any of the preceding embodiments, detecting a rolling circle amplification product can comprise: contacting the biological sample with one or more detectably-labeled probes that directly or indirectly hybridize to the rolling circle amplification product, and dehybridizing the one or more detectably-labeled probes from the rolling circle amplification product. In some embodiments, the contacting and dehybridizing steps are repeated with the one or more detectably-labeled probes and/or one or more other detectably-labeled probes that directly or indirectly hybridize to the rolling circle amplification product.

In any of the preceding embodiments, detecting a rolling circle amplification product can comprise: contacting the biological sample with one or more intermediate probes that directly or indirectly hybridize to the rolling circle amplification product, wherein the one or more intermediate probes are detectable using one or more detectably-labeled probes, and dehybridizing the one or more intermediate probes and/or the one or more detectably-labeled probes from the rolling circle amplification product. In some embodiments, the contacting and dehybridizing steps are repeated with the one or more intermediate probes, the one or more detectably-labeled probes, one or more other intermediate probes, and/or one or more other detectably-labeled probes.

In any of the preceding embodiments, the detectably-labeled probes and/or the intermediate probes can hybridize to barcode sequences or complements thereof in the rolling circle amplification products.

In any of the preceding embodiments, the circular nucleic acid can be formed in the biological sample from a probe or a probe set for a target molecule. In any of the preceding embodiments, the circular nucleic acid can be formed in the biological sample from a padlock probe, a SNAIL (specific amplification of nucleic acids via intramolecular ligation) probe set, a PLAYR (proximity ligation assay for RNA) probe set, and a PLISH (proximity ligation in situ hybridization) probe set.

In any of the preceding embodiments, the target molecule can be a target nucleic acid. In any of the preceding embodiments, the target molecule can comprise a viral DNA, bacterial DNA, or cellular DNA or RNA molecule or a product thereof in the biological sample. In any of the preceding embodiments, the target molecule can comprise a probe that binds to a viral DNA, bacterial DNA, or cellular DNA or RNA molecule or a product thereof in the biological sample. In any of the preceding embodiments, the target molecule can comprise a product of a probe that binds to a viral DNA, bacterial DNA, or cellular DNA or RNA molecule or a product thereof in the biological sample. In any of the preceding embodiments, the target molecule can comprise genomic DNA, mitochondrial DNA, mRNA or cDNA, and the probe or probe set for the target molecule can comprise a padlock probe that hybridizes to the genomic DNA, mitochondrial DNA, mRNA or cDNA. In any of the preceding embodiments, the method can comprise ligating the padlock probe hybridized to the genomic DNA, mitochondrial DNA, mRNA or cDNA to form the circular nucleic acid.

In any of the preceding embodiments, the target molecule can be a non-nucleic acid target molecule. In any of the preceding embodiments, the target molecule can be a target protein. In any of the preceding embodiments, the method can comprise contacting the biological sample with a labelling agent comprising (i) a binding moiety that that directly or indirectly binds to the non-nucleic acid target molecule and (ii) a reporter oligonucleotide that corresponds to the binding moiety and/or the non-nucleic acid target molecule. In any of the preceding embodiments, the probe or probe set for the non-nucleic acid target molecule can comprise a padlock probe that hybridizes to the reporter oligonucleotide. In any of the preceding embodiments, the method can comprise ligating the padlock probe hybridized to the reporter oligonucleotide to form the circular nucleic acid.

In some aspects, provided herein is a method for analyzing a biological sample, comprising: contacting the biological sample with a binding mixture, wherein the biological sample comprises a plurality of circular nucleic acids each comprising a primer hybridization region, the binding mixture comprises a plurality of complexes each comprising a polymerase bound to a primer, wherein the primer comprises a sequence complementary to the primer hybridization region of one or more circular nucleic acids, and the polymerase activity of the polymerase is inhibited, thereby allowing the plurality of complexes to hybridize to the plurality of circular nucleic acids. In some embodiments, the method further comprises contacting the biological sample with a primer extension reaction mixture to allow the polymerase to extend the primer hybridized to the primer hybridization region, thereby synchronizing rolling circle amplification the plurality of circular nucleic acids in the biological sample.

In any of the preceding embodiments, the binding mixture can comprise a chelating agent. In any of the preceding embodiments, the binding mixture may contain one or more deoxynucleoside triphosphates (dNTPs). Alternatively, in any of the preceding embodiments, the binding mixture may be substantially free of dNTPs.

In any of the preceding embodiments, the primer in one or more of the complexes may have a 3' hydroxyl group. In any of the preceding embodiments, the primer in one or more of the complexes may have a thiophosphate-protected 3' nucleotide, thereby protecting the primer from 3'→5' exonuclease degradation by the polymerase in the complex while allowing priming by the polymerase. In any of the preceding embodiments, the primer hybridization regions in two or more of the plurality of circular nucleic acids can be the same in sequence. In any of the preceding embodiments, the primer hybridization regions in two or more of the plurality of circular nucleic acids can be different in sequence. In any of the preceding embodiments, the primers in two or more of the plurality of complexes can be the same in sequence. In any of the preceding embodiments, the primers in two or more of the plurality of complexes can be different in sequence. In any of the preceding embodiments, the polymerase can be a Phi29 DNA polymerase, a Bst polymerase, a T7 RNA polymerase, or a Klenow fragment. In any of the preceding embodiments, the method may further comprise, between the contacting steps, removing one or more complexes not bound to the circular nucleic acid(s) from the biological sample. In any of the preceding embodiments, the primer extension reaction mixture can comprise deoxynucleoside triphosphates (dNTPs) and one or more cations. In any of the preceding embodiments, the primer extension reaction mixture can comprise $Mg^{2+}$, $Co^{2+}$, and/or $Mn^{2+}$. In any of the preceding embodiments, the primer extension reaction mixture may not comprise the polymerase.

In some aspects, provided herein is a method for analyzing a biological sample, comprising: contacting the biological sample with a binding mixture, wherein the biological sample comprises a plurality of circular nucleic acids each comprising a hybridization region hybridized to a polynucleotide, the binding mixture comprises a polymerase, and the polymerase activity of the polymerase is inhibited, thereby allowing the polymerase to bind to the plurality of circular nucleic acids; and contacting the biological sample with a primer extension reaction mixture to allow the polymerase to extend the polynucleotide hybridized to the hybridization region, thereby synchronizing rolling circle amplification of the plurality of circular nucleic acids in the biological sample.

In any of the preceding embodiments, the polynucleotide can be an exogenous primer contacted with the biological sample, the hybridization region can be a primer hybridization region, and the circular nucleic acids can comprise (i) endogenous molecules in the biological sample, (ii) products of endogenous molecules in the biological sample, (iii) probes targeting endogenous molecules in the biological sample, and/or (iv) products of exogenous probes targeting endogenous molecules in the biological sample.

In any of the preceding embodiments, the polynucleotide comprises (i) an endogenous molecule in the biological sample, (ii) a product of an endogenous molecule in the biological sample, (iii) a probe targeting an endogenous molecule in the biological sample, and/or (iv) a product of an exogenous probe targeting an endogenous molecule in the biological sample.

In any of the preceding embodiments, the method can further comprise terminating rolling circle amplification (RCA) of the circular nucleic acids to provide a plurality of rolling circle amplification products.

In any of the preceding embodiments, the plurality of rolling circle amplification products can have a mean diameter of about 0.05 μm, about 0.1 μm, about 0.2 μm, about 0.3 μm, about 0.4 μm, about 0.5 μm, about 0.6 μm, about 0.7 μm, about 0.8 μm, about 0.9 μm, about 1.0 μm, about 1.1 μm, about 1.2 μm, about 1.3 μm, about 1.4 μm, or about 1.5 μm, or between any of the aforementioned values. In any of the preceding embodiments, the plurality of rolling circle amplification products can have a mean diameter smaller than 0.25 μm.

In any of the preceding embodiments, the plurality of rolling circle amplification products can have a mean length of about 1 kb, about 2 kb, about 5 kb, about 10 kb, about 20 kb, about 30 kb, about 40 kb, about 50 kb, about 60 kb, or about 70 kb, or between any of the aforementioned values. In any of the preceding embodiments, the plurality of rolling circle amplification products can have a mean length less than 20 kb or less than 10 kb.

In any of the preceding embodiments, the mean number of copies of a unit sequence complementary to the circular nucleic acid in the plurality of rolling circle amplification products can be about 10, about 50, about 100, about 500, about 1,000, about 5,000, or about 10,000 or more.

In any of the preceding embodiments, the mean number of copies of a unit sequence complementary to the circular nucleic acid in the plurality of rolling circle amplification products can be less than 100 or less than 1,000.

In any of the preceding embodiments, the mean peak intensity value of the plurality of rolling circle amplification products can be between about 2 and about 10 times greater than a mean peak intensity value of rolling circle amplification products formed without synchronizing rolling circle amplification of the plurality of circular nucleic acids in the biological sample.

In any of the preceding embodiments, the distribution of the relative observed signal of rolling circle amplification products formed with synchronizing rolling circle amplification of the plurality of circular nucleic acids in the biological sample may be narrower than the distribution of the relative observed signal of rolling circle amplification products formed without synchronizing rolling circle amplification of the plurality of circular nucleic acids in the biological sample.

In any of the preceding embodiments, the polymerase extension may be performed for no more than 3 hours. In any of the preceding embodiments, the polymerase extension may be performed for no more than 2 hours. In any of the preceding embodiments, the polymerase extension may be performed for no more than 1 hours. In any of the preceding embodiments, the polymerase extension may be performed for no more than 30 minutes.

In some embodiments, disclosed herein is a kit for analyzing a biological sample, comprising: (i) a binding mixture comprising a plurality of complexes each comprising a polymerase bound to a primer, and a chelating agent, wherein the binding mixture is substantially free of deoxynucleoside triphosphates (dNTPs); and (ii) a primer extension reaction mixture comprising dNTPs and a di-cation, wherein the primer extension reaction mixture is substantially free of the polymerase. In any of the preceding embodiments, the primers in the plurality of complexes may be the same. Alternatively, in any of the preceding embodiments, the primers in two or more of the plurality of complexes can be different. In any of the preceding embodiments, the polymerase can be Phi29 DNA polymerase and the di-cation can be $Mg^{2+}$, $Co^{2+}$, and/or $Mn^2$.

In any of the preceding embodiments, the biological sample can comprise cells or cellular components. In any of the preceding embodiments, the biological sample can be a tissue sample. In any of the preceding embodiments, the biological sample can be fixed. Alternatively, in any of the preceding embodiments, the biological sample may not be fixed. In any of the preceding embodiments, the biological sample can be a formalin-fixed, paraffin-embedded (FFPE) sample, a frozen tissue sample, or a fresh tissue sample. In any of the preceding embodiments, the biological sample can be permeabilized. In any of the preceding embodiments, the biological sample can be processed. In any of the preceding embodiments, the biological sample can be cleared. In any of the preceding embodiments, the biological sample can be embedded in a matrix. In any of the preceding embodiments, the biological sample can be embedded in a hydrogel. In any of the preceding embodiments, the biological sample can be embedded in a hydrogel and then cleared. In any of the preceding embodiments, the biological sample and/or the matrix can be crosslinked. In any of the preceding embodiments, the biological sample can be immobilized on a substrate, such as a glass or plastic slide.

BRIEF DESCRIPTION OF THE DRAWINGS

The drawings illustrate certain embodiments of the features and advantages of this disclosure. These embodiments are not intended to limit the scope of the appended claims in any manner.

FIG. 4A shows trends of enhanced intensity under synchronized conditions ("synch") relative to the control group ("ctrl") for 60 minutes RCA and 120 minutes RCA. FIG. 4B shows representative images of features detected after 120 minutes of amplification, showing a trend toward more uniformity in feature intensity in the synchronized groups as compared to the control group.

FIG. 4C shows representative images after feature detection and filtering in the control and synchronized groups with 30 minutes of RCA, showing a trend of improved detection of RCA products at the locations where Slc17a7 expression is expected in the brain tissue.

DETAILED DESCRIPTION

Figure 1A:
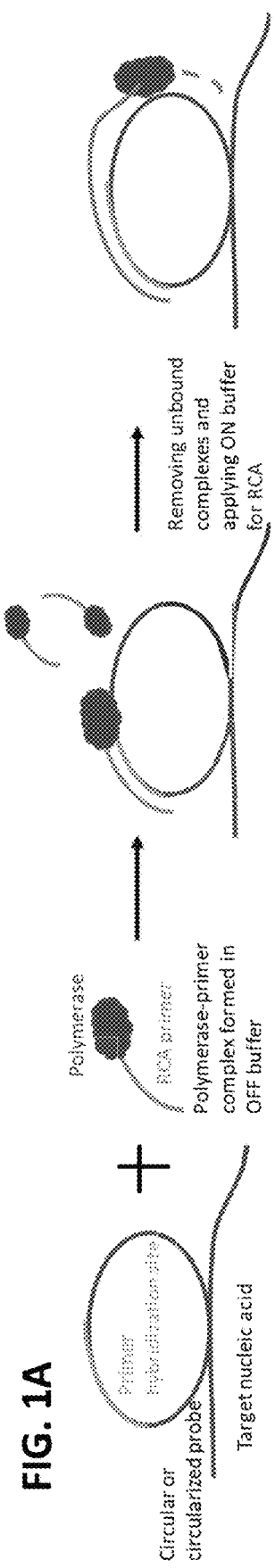
FIGS. 1A-1C show schematics of exemplary methods of synchronizing RCA in situ. A circular or circularized probe hybridized to a target nucleic acid in a sample may comprise a primer hybridization site. A complex of a polymerase (e.g., Phi29) and a primer may be formed in an OFF buffer that inhibits the polymerase activity of the polymerase. The preformed polymerase-primer complex can diffuse in the sample and hybridize to the primer hybridization site. The hybridization of the preformed complexes to target nucleic acid molecules at different locations in the sample can be synchronized, while RCA does not begin until unbound complexes are removed and an ON buffer is applied to initiate RCA at the different locations (FIG. 1A). Alternatively, primers may be hybridized to circular or circularized probes at different locations in the sample, which is then contacted with a polymerase (e.g., Phi29) in an OFF buffer that inhibits the polymerase activity. The polymerase can diffuse in the sample and bind to the primers hybridized on the circular or circularized probes. RCA does not begin until unbound polymerases are removed and an ON buffer is applied to initiate RCA at the different locations (FIG. 1B). In another example, a circular or circularized probe is hybridized to a polynucleotide in a sample, which is then contacted with a polymerase (e.g., Phi29) in an OFF buffer that inhibits the polymerase activity. RCA does not begin until unbound polymerases are removed and an ON buffer is applied to initiate RCA at the different locations using the polynucleotide as the RCA primer (FIG. 1C). In this example, the polynucleotide can be any endogenous or exogenous nucleic acid (or product thereof) in the sample, for example, mRNA or cDNA, and no separate RCA primer is necessary.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

In assays involving in situ rolling circle amplification (RCA), the heterogeneous size and intensity distribution of rolling circle amplification products can lead to loss of sensitivity, because weak signals associated with certain rolling circle amplification products may not pass the detection threshold of spot detection for image analysis, while strong signals associated with certain rolling circle amplification products in close proximity may lead to optical crowding as well as the inability to detect nearby weaker signal spots. Both weak undetected rolling circle amplification products and large overcrowding rolling circle amplification products can lead to loss of sensitivity. In some aspects, the heterogeneous size and intensity distribution may be due to RCA reactions starting at different times in situ in a unsynchronized manner. In some aspects, the heterogeneity may result from the diffusion time and speed of one or more reagents (e.g., enzyme, primer, etc.) through a sample (e.g., a tissue section) to different locations in the sample. In some cases, when a polymerase such as phi29 is added in an RCA reaction buffer and applied to a sample, the enzyme diffuses from bulk solution through the sample (e.g., a tissue section) to a primer and a circular template in the sample in order to start an RCA reaction. As such, circular templates that receive a functional polymerase molecule at a later time may start with RCA at later time than other circular templates that have received a polymerase molecule earlier. When RCA is stopped at the same time point, circular templates that have initiated earlier have resulted in larger and brighter signal spots associated with the rolling circle amplification products, while circular templates that have initiated at later time points have generated smaller and weaker signal spots.

In some aspects, provided herein are compositions and methods for generating rolling circle amplification products by synchronizing the RCA starting point to achieve greater homogeneity in size of the RCA products. In some aspects, provided herein are compositions and methods for generating in situ RCA products that are more homogeneous in size and intensity in order to make spot detection more robust for image analysis. In some cases, the advantages of synchronizing RCA may be applicable to a biological sample with highly expressed genes to be detected. In some embodiments, a polymerase such as Phi29 is used to bind single-stranded nucleic acid (e.g., ssDNA) in a polynucleotide (e.g., a probe or a target nucleic acid such as mRNA or cDNA) with its single-stranded nucleic acid binding domain, while its exonuclease and polymerase functions are disabled in an OFF buffer, e.g., a binding buffer that is substantially free of one or more cofactors (e.g., $Mg^{2+}$) and/or dNTPs. In some embodiments, complexes of RCA primers and polymerases (e.g., Phi29) are preformed in an OFF buffer. In some embodiments, the complexes are then added to a sample such as a tissue section with preformed circle templates (e.g., made through padlock probe ligation on a target nucleic acid).

Figure 1B:
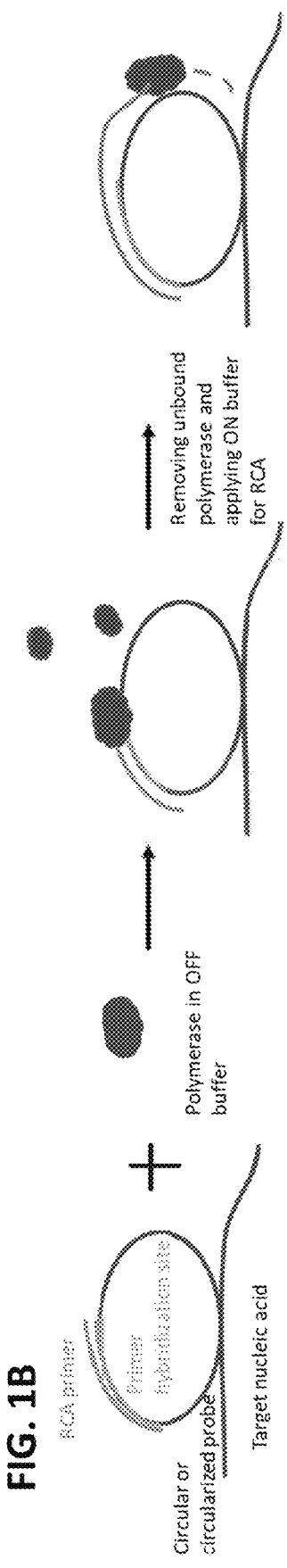
Figure 1C:
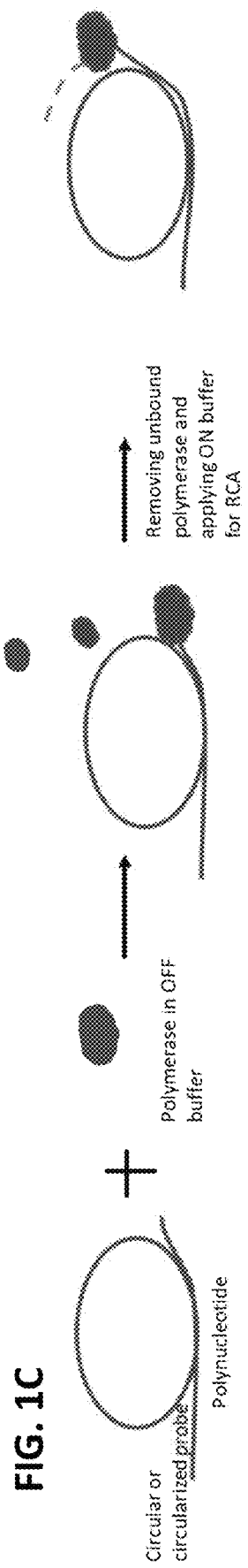

In some embodiments, after hybridization of the complex to the RCA primer sites in the circle (e.g., circular nucleic acid), the mixture is removed and replaced with an ON buffer, which activates the polymerase and initiates RCA in the RCA reaction mixture simultaneously for all circles that have received a polymerase-primer complex (FIG. 1A). In some aspects, primers are pre-hybridized to circular templates in a sample. In some embodiments, a polymerase such as Phi29 is provided in an OFF buffer that inhibits one or more activities of the polymerase, and then contacted with the sample. The polymerase binds to the primers pre-hybridized to circular templates, but RCA is not initiated until the sample is contacted with an ON buffer (e.g., an RCA reaction buffer) that lifts the inhibition on the polymerase and/or exonuclease activities of the polymerase, thereby synchronizing RCA from circular templates at multiple locations in the sample (FIG. 1B). In some embodiments, polymerases can be loaded onto a sample with circular nucleic acid molecules, where no separate RCA primer is provided. For instance, in one embodiment, a polymerase in an OFF buffer is applied to a sample and binds to the 3' end of a polynucleotide (e.g., RNA or DNA, such as mRNA or cDNA) in the sample. In some embodiments, the polymerases loaded onto the polynucleotides in the sample can be activated with an ON buffer to use the polynucleotides as primers to prime synchronized RCA reactions (FIG. 1C).

In some embodiments, the synchronization leads to more homogeneously sized RCA products and/or brighter signal spots for the RCA products. In some embodiments, the synchronization leads to fewer dim signal spots and/or more bright signal spots for the RCA products. In some embodiments, when RCA product size becomes more homogeneous, the amplification time can be decreased, which makes smaller, but similarly bright RCA products. Overall, the synchronization can facilitate the detection and/or resolving of more RCA products in a crowded space.

II. Samples, Analytes, and Target Sequences

A. Samples

A sample disclosed herein can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding.

Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or padlock probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a padlock probe.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively any other hydrogel-formation method may be utilized.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 m to about 2 mm.

Additional methods and aspects of hydrogel embedding of biological samples are described for example in Chen et al., Science 347(6221):543-548, 2015, the entire contents of which are incorporated herein by reference.

(v) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DiR, DiD). Other cell membrane stains may include FM and RH dyes or immunohistochemical reagents specific for cell membrane proteins. In some examples, the stain may include, but is not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation.

In some embodiments, the sample can be stained using Romanowsky stain, including Wright's stain, Jenner's stain, Can-Grunwald stain, Leishman stain, and Giemsa stain.

In some embodiments, biological samples can be destained. Any suitable method of destaining or discoloring a biological sample may be utilized, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015, the entire contents of which are incorporated herein by reference.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., *Nat. Methods* 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay round. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively any other hydrogel-formation method may be utilized. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of analytes out of the sample, and/or to facilitate transfer of species (such as probes) into the sample. If a sample is not permeabilized sufficiently, the amount of species (such as probes) in the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to opening up DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

In some embodiments, an oligonucleotide with sequence complementarity to the complementary strand of RNA (e.g., cDNA) can bind to the cDNA. For example, biotinylated oligonucleotides with sequence complementary to one or more cDNA of interest binds to the cDNA and biotinylation-strepavidin affinity methods may be utilized to capture the biotinylated oligonucleotides (e.g., using streptavidin beads).

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics*, 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, Biotechniques, 53(6) 373-80, (2012), the entire contents of which are incorporated herein by reference).

A biological sample may comprise one or a plurality of analytes of interest. Methods for performing multiplexed assays to analyze two or more different analytes in a single biological sample are provided.

B. Analytes

The methods and compositions disclosed herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g. a padlock or other circularizable probe). Alternatively, the specific binding partner may be coupled to a nucleic acid, which may be detected using an RCA strategy, e.g. in an assay which uses or generates a circular nucleic acid which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

(i) Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, generated in the sample, added to the sample, or associated with an analyte in the sample. In some embodiments, the target sequence is a single-stranded target sequence (e.g., a sequence in a rolling circle amplification product). In some embodiments, the analytes comprise one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

(ii) Labelling Agents

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such as a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence, a primer or primer binding sequence, a sequencing primer or primer biding sequence.

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (e.g., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

(iii) Products of Endogenous Analyte and/or Labelling Agent

In some embodiments, provided herein are methods and compositions for analyzing one or more products of an endogenous analyte and/or a labelling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product such as a rolling circle amplification (RCA) product) thereof is analyzed. In some embodiments, a labelling agent that directly or indirectly binds to an analyte in the biological sample is analyzed. In some embodiments, a product (e.g., a hybridization product, a ligation product, an extension product (e.g., by a DNA or RNA polymerase), a replication product, a transcription/reverse transcription product, and/or an amplification product such as a rolling circle amplification (RCA) product) of a labelling agent that directly or indirectly binds to an analyte in the biological sample is analyzed.

(a) Hybridization

In some embodiments, a product of an endogenous analyte and/or a labelling agent is a hybridization product comprising the pairing of substantially complementary or complementary nucleic acid sequences within two different molecules, one of which is the endogenous analyte or the labelling agent (e.g., reporter oligonucleotide attached thereto). The other molecule can be another endogenous molecule or another labelling agent such as a probe. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

Various probes and probe sets can be hybridized to an endogenous analyte and/or a labelling agent and each probe may comprise one or more barcode sequences. Exemplary barcoded probes or probe sets may be based on a padlock probe, a gapped padlock probe, a SNAIL (Splint Nucleotide Assisted Intramolecular Ligation) probe set, a PLAYR (Proximity Ligation Assay for RNA) probe set, and a PLISH (Proximity Ligation in situ Hybridization) probe set. The specific probe or probe set design can vary.

(b) Ligation

In some embodiments, a product of an endogenous analyte and/or a labelling agent is a ligation product. In some embodiments, the ligation product is formed between two or more endogenous analytes. In some embodiments, the ligation product is formed between an endogenous analyte and a labelling agent. In some embodiments, the ligation product is formed between two or more labelling agent. In some embodiments, the ligation product is an intramolecular ligation of an endogenous analyte. In some embodiments, the ligation product is an intramolecular ligation of a labelling agent, for example, the circularization of a circularizable probe or probe set upon hybridization to a target sequence. The target sequence can be comprised in an endogenous analyte (e.g., nucleic acid such as a genomic DNA or mRNA) or a product thereof (e.g., cDNA from a cellular mRNA transcript), or in a labelling agent (e.g., the reporter oligonucleotide) or a product thereof.

In some embodiments, provided herein is a probe or probe set capable of DNA-templated ligation, such as from a cDNA molecule. See, e.g., U.S. Pat. No. 8,551,710, which is hereby incorporated by reference in its entirety. See, e.g., U.S. Pat. Pub. 2020/0224244 which is hereby incorporated by reference in its entirety. In some embodiments, the probe set is a SNAIL probe set. See, e.g., U.S. Pat. Pub. 20190055594, which is hereby incorporated by reference in its entirety. In some embodiments, provided herein is a multiplexed proximity ligation assay. See, e.g., U.S. Pat. Pub. 20140194311 which is hereby incorporated by reference in its entirety. In some embodiments, provided herein is a probe or probe set capable of proximity ligation, for instance a proximity ligation assay for RNA (e.g., PLAYR) probe set. See, e.g., U.S. Pat. Pub. 20160108458, which is hereby incorporated by reference in its entirety. In some embodiments, a circular probe can be indirectly hybridized to the target nucleic acid. In some embodiments, the circular construct is formed from a probe set capable of proximity ligation, for instance a proximity ligation in situ hybridization (PLISH) probe set. See, e.g., U.S. Pat. Pub. 2020/0224243 which is hereby incorporated by reference in its entirety.

In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, e.g., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, padlock probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(c) Primer Extension and Amplification

In some embodiments, a product is a primer extension product of an analyte, a labelling agent, a circularizable probe or probe set bound to the analyte (e.g., a padlock probe bound to genomic DNA, mRNA, or cDNA), or a circularizable probe or probe set bound to the labelling agent (e.g., a padlock probe bound to one or more reporter oligonucleotides from the same or different labelling agents).

In some embodiments, a primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence. In some embodiments, a primer extension reaction generally refers to any method where two nucleic acid sequences become linked (e.g., hybridized) by an overlap of their respective terminal complementary nucleic acid sequences (e.g., 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some embodiments, a product of an endogenous analyte and/or a labelling agent is an amplification product of one or more polynucleotides, for instance, a circular probe or circularizable probe or probe set. In some embodiments, the amplifying is achieved by performing rolling circle amplification (RCA). In other embodiments, a primer that hybridizes to the circular probe or circularized probe is added and used as such for amplification. In some embodiments, the RCA comprises a linear RCA, a branched RCA, a dendritic RCA, or any combination thereof.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (e.g., amplicon) containing multiple copies of the cDNA. Techniques for rolling circle amplification (RCA) include linear RCA, a branched RCA, a dendritic RCA, or any combination thereof. (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29:el 18, 2001; Dean et al. Genome Res. 1 1:1095-1099, 2001; Schweitzer et al, Nature Biotech. 20:359-365, 2002; U.S. Pat. Nos. 6,054,274, 6,291,187, 6,323,009, 6,344,329 and 6,368,801, all of which are herein incorporated by reference in their entireties). Exemplary polymerases for use in RCA comprise DNA polymerase such phi29 ($\varphi^{29}$) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, WO 2014/163886, WO 2017/079406, US 2016/0024555, US 2018/0251833 and US 2017/0219465, all of which are herein incorporated by reference in their entireties. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

In some embodiments, the RCA template may comprise the target analyte, or a part thereof, where the target analyte is a nucleic acid, or it may be provided or generated as a proxy, or a marker, for the analyte. As noted above, many assays may be utilized for the detection of numerous different analytes, which use a RCA-based detection system, e.g., where the signal is provided by generating a RCA product from a circular RCA template which is provided or generated in the assay, and the RCA product is detected to detect the analyte. The RCA product may thus be regarded as a reporter which is detected to detect the target analyte. However, the RCA template may also be regarded as a reporter for the target analyte; the RCA product is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (e.g. a reagent in a detection assay), which is used as a reporter for the assay, or a part of a reporter, or signal-generation system. The RCA template used to generate the RCA product may thus be a circular (e.g. circularized) reporter nucleic acid molecule, namely from any RCA-based detection assay which uses or generates a circular nucleic acid as a reporter for the assay.

In some embodiments, a product herein includes a molecule or a complex generated in a series of reactions, e.g., hybridization, ligation, extension, replication, transcription/reverse transcription, and/or amplification (e.g., rolling circle amplification), in any suitable combination. For example, a product comprising a target sequence for a probe disclosed herein may be a hybridization complex formed of a cellular nucleic acid in a sample and an exogenously added nucleic acid probe. The exogenously added nucleic acid probe may comprise an overhang that does not hybridize to the cellular nucleic acid but hybridizes to another probe. The exogenously added nucleic acid probe may be optionally ligated to a cellular nucleic acid molecule or another exogenous nucleic acid molecule. In other examples, a product comprising a target sequence for a probe disclosed herein may be an RCA product of a circularizable probe or probe set which hybridizes to a cellular nucleic acid molecule (e.g., genomic DNA or mRNA) or product thereof (e.g., a transcript such as cDNA, or a templated ligation product of two probes). In other examples, a product comprising a target sequence for a probe (e.g., a detectably labeled probe) disclosed herein may be a probe (e.g., an intermediate probe such as an L-shaped probe) hybridizing to an RCA product. The probe (e.g., intermediate probe) may comprise an overhang that does not hybridize to the RCA product but hybridizes to another probe. The probe may be optionally ligated to a cellular nucleic acid molecule or another probe, e.g., an anchor probe that hybridize to the RCA product.

C. Target Sequences

A target sequence for a probe disclosed herein may be comprised in any analyte disclose herein, including an endogenous analyte (e.g., a viral or cellular nucleic acid), a labelling agent, or a product of an endogenous analyte and/or a labelling agent.

In some aspects, one or more of the target sequences includes one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In any of the preceding embodiments, barcodes (e.g., primary and/or secondary barcode sequences) can be analyzed (e.g., detected or sequenced) using any suitable methods or techniques, including those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), in situ sequencing, hybridization-based in situ sequencing (HybISS), targeted in situ sequencing, fluorescent in situ sequencing (FISSEQ), sequencing by synthesis (SBS), sequencing by ligation (SBL), sequencing by hybridization (SBH), or spatially-resolved transcript amplicon readout mapping (STARmap). In any of the preceding embodiments, the methods provided herein can include analyzing the barcodes by sequential hybridization and detection with a plurality of labelled probes (e.g., detection oligos).

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence (45=1024), whereas 8 nucleotide barcodes can be used to identify up to 65,536 molecular species, a number greater than the total number of distinct genes in the human genome. In some embodiments, the barcode sequences contained in the probes or RCA products are detected, rather than endogenous sequences, which can be an efficient readout in terms of information per cycle of sequencing. Because the barcode sequences are pre-determined, they can also be designed to feature error detection and correction mechanisms, see, e.g., U.S. Pat. Pub. 20190055594 and U.S. Pat. Pub. 20210164039, which are hereby incorporated by reference in their entirety.

III. Nucleic Acid Probes

Disclosed herein in some aspects are nucleic acid probes and/or probe sets that are introduced into a cell or used to otherwise contact a biological sample such as a tissue sample. The probes may comprise any of a variety of entities that can hybridize to a nucleic acid, typically by Watson-Crick base pairing, such as DNA, RNA, LNA, PNA, etc. The nucleic acid probe typically contains a targeting sequence that is able to directly or indirectly bind to at least a portion of a target nucleic acid. For example, the nucleic acid probe is a circular nucleic acid or is used to generate a circular nucleic acid comprising a hybridization region complementary to a polynucleotide (e.g., amplification primer). The nucleic acid probe may be able to bind to a specific target nucleic acid (e.g., an mRNA, or other nucleic acids as discussed herein). In some embodiments, the nucleic acid probes may be detected using a detectable label, and/or by using secondary nucleic acid probes able to bind to the nucleic acid probes. In some embodiments, the nucleic acid probes (e.g., primary probes and/or secondary probes) are compatible with one or more biological and/or chemical reactions. For instance, a nucleic acid probe disclosed herein can serve as a template or primer for a polymerase, a template or substrate for a ligase, a substrate for a click chemistry reaction, and/or a substrate for a nuclease (e.g., endonuclease or exonuclease for cleavage or digestion).

In some embodiments, more than one type of primary nucleic acid probes may be contacted with a sample, e.g., simultaneously or sequentially in any suitable order, such as in sequential probe hybridization/unhybridization cycles. In some embodiments, the primary probes may comprise circular probes and/or circularizable probes (such as padlock probes). In some embodiments, more than one type of secondary nucleic acid probes may be contacted with a sample, e.g., simultaneously or sequentially in any suitable order, such as in sequential probe hybridization/unhybridization cycles. In some embodiments, the secondary probes may comprise intermediate probes that bind to a product (e.g., an RCA product) of a primary probe targeting an analyte. In some embodiments, more than one type of higher order nucleic acid probes may be contacted with a sample, e.g., simultaneously or sequentially in any suitable order, such as in sequential probe hybridization/unhybridization cycles. In some embodiments, more than one type of detectably labeled nucleic acid probes may be contacted with a sample, e.g., simultaneously or sequentially in any suitable order, such as in sequential probe hybridization/unhybridization cycles. In some embodiments, the detectably labeled probes may comprise probes that bind to one or more primary probes, one or more secondary probes, one or more higher order probes, one or more intermediate probes between a primary/second/higher order probes, and/or one or more detectably or non-detectably labeled probes (e.g., as in the case of a hybridization chain reaction (HCR), a branched DNA reaction (bDNA), or the like). In some embodiments, at least 2, at least 5, at least 10, at least 25, at least 50, at least 75, at least 100, at least 300, at least 1,000, at least 3,000, at least 10,000, at least 30,000, at least 50,000, at least 100,000, at least 250,000, at least 500,000, or at least 1,000,000 distinguishable nucleic acid probes (e.g., primary, secondary, higher order probes, and/or detectably labeled probes) can be contacted with a sample, e.g., simultaneously or sequentially in any suitable order. Between any of the probe contacting steps disclosed herein, the method may comprise one or more intervening reactions and/or processing steps, such as modifications of a target nucleic acid, modifications of a probe or product thereof (e.g., via hybridization, ligation, extension, amplification, cleavage, digestion, branch migration, primer exchange reaction, click chemistry reaction, crosslinking, attachment of a detectable label, activating photo-reactive moieties, etc.), removal of a probe or product thereof (e.g., cleaving off a portion of a probe and/or unhybridizing the entire probe), signal modifications (e.g., quenching, masking, photo-bleaching, signal enhancement (e.g., via FRET), signal amplification, etc.), signal removal (e.g., cleaving off or permanently inactivating a detectable label), crosslinking, de-crosslinking, and/or signal detection.

The target-binding sequence (sometimes also referred to as the targeting region/sequence or the recognition region/sequence) of a probe may be positioned anywhere within the probe. For instance, the target-binding sequence of a primary probe that binds to a target nucleic acid can be 5' or 3' to any barcode sequence in the primary probe. Likewise, the target-binding sequence of a secondary probe (which binds to a primary probe or complement or product thereof) can be 5' or 3' to any barcode sequence in the secondary probe. In some embodiments, the target-binding sequence may comprise a sequence that is substantially complementary to a portion of a target nucleic acid. In some embodiments, the portions may be at least 50%, at least 60%, at least 70%, at least 75%, at least 80%, at least 85%, at least 90%, at least 92%, at least 94%, at least 95%, at least 96%, at least 97%, at least 98%, at least 99%, or 100% complementary.

The target-binding sequence of a primary nucleic acid probe may be determined with reference to a target nucleic acid (e.g., a cellular RNA or a reporter oligonucleotide of a labelling agent for a cellular analyte) that is present or suspected of being present in a sample. In some embodiments, more than one target-binding sequence can be used to identify a particular analyte comprising or associated with a target nucleic acid. The more than one target-binding sequence can be in the same probe or in different probes. For instance, multiple probes can be used, sequentially and/or simultaneously, that can bind to (e.g., hybridize to) different regions of the same target nucleic acid. In other examples, a probe may comprise target-binding sequences that can bind to different target nucleic acid sequences, e.g., various intron and/or exon sequences of the same gene (for detecting splice variants, for example), or sequences of different genes, e.g., for detecting a product that comprises the different target nucleic acid sequences, such as a genome rearrangement (e.g., inversion, transposition, translocation, insertion, deletion, duplication, and/or amplification).

After contacting the nucleic acid probes with a sample, the probes may be directly detected by determining detectable labels (if present), and/or detected by using one or more other probes that bind directly or indirectly to the probes or products thereof. The one or more other probes may comprise a detectable label. For instance, a primary nucleic acid probe can bind to a target nucleic acid in the sample, and a secondary nucleic acid probe can be introduced to bind to an amplification product of the primary nucleic acid probe, where the secondary nucleic acid probe or a product thereof can then be detected using detectably labeled probes. Higher order probes that directly or indirectly bind to the secondary nucleic acid probe or product thereof may also be used, and the higher order probes or products thereof can then be detected using detectably labeled probes.

In some embodiments, the detection may be spatial, e.g., in two or three dimensions. In some embodiments, the detection may be quantitative, e.g., the amount or concentration of a primary nucleic acid probe (and of a target nucleic acid) may be determined. In some embodiments, the primary probes, secondary probes, higher order probes, and/or detectably labeled probes may comprise any of a variety of entities able to hybridize a nucleic acid, e.g., DNA, RNA, LNA, and/or PNA, etc., depending on the application.

A secondary nucleic acid probe (e.g., intermediate probe) may contain a recognition sequence able to bind to or hybridize with a primary nucleic acid probe or a product thereof, e.g., at a barcode sequence or portion(s) thereof of the primary nucleic acid probe, or at a complement of the barcode sequence or portion(s) thereof (e.g., in the case of the secondary probe hybridizing to an RCA product of the primary probe). In some embodiments, a secondary nucleic acid probe may bind to a combination of barcode sequences (which may be continuous or spaced from one another) in a primary nucleic acid probe or a product thereof. In some embodiments, the binding is specific, or the binding may be such that a recognition sequence preferentially binds to or hybridizes with only one of the barcode sequences or complements thereof that are present. The secondary nucleic acid probe may also contain one or more detectable labels. If more than one secondary nucleic acid probe is used, the detectable labels may be the same or different.

The recognition sequences may be of any length, and multiple recognition sequences in the same or different secondary nucleic acid probes may be of the same or different lengths. If more than one recognition sequence is used, the recognition sequences may independently have the same or different lengths. For instance, the recognition sequence may be at least 4, at least 5, least 6, least 7, least 8, least 9, at least 10, least 11, least 12, least 13, least 14, at least 15, least 16, least 17, least 18, least 19, at least 20, at least 25, at least 30, at least 35, at least 40, or at least 50 nucleotides in length. In some embodiments, the recognition sequence may be no more than 48, no more than 40, no more than 32, no more than 24, no more than 16, no more than 12, no more than 10, no more than 8, or no more than 6 nucleotides in length. Combinations of any of these are also possible, e.g., the recognition sequence may have a length of between 5 and 8, between 6 and 12, or between 7 and 15 nucleotides, etc. In one embodiment, the recognition sequence is of the same length as a barcode sequence or complement thereof of a primary nucleic acid probe or a product thereof. In some embodiments, the recognition sequence may be at least 50%, at least 60%, at least 70%, at least 75%, at least 80%, at least 85%, at least 90%, at least 92%, at least 94%, at least 95%, at least 96%, at least 97%, at least 98%, at least 99%, or at least 100% complementary to the barcode sequence or complement thereof.

In some embodiments, a nucleic acid probe, such as a primary or a secondary nucleic acid probe, may also comprise 1, 2, 3, 4, 5, 6, 7, 8, 9, 10, 11, 12, 13, 14, 15 or more, 20 or more, 32 or more, 40 or more, or 50 or more barcode sequences. The barcode sequences may be positioned anywhere within the nucleic acid probe. If more than one barcode sequences are present, the barcode sequences may be positioned next to each other, and/or interspersed with other sequences. In some embodiments, two or more of the barcode sequences may also at least partially overlap. In some embodiments, two or more of the barcode sequences in the same probe do not overlap. In some embodiments, all of the barcode sequences in the same probe are separated from one another by at least a phosphodiester bond (e.g., they may be immediately adjacent to each other but do not overlap), such as 1, 2, 3, 4, 5, 6, 7, 8, 9, 10 or more nucleotides apart.

The barcode sequences, if present, may be of any length. If more than one barcode sequence is used, the barcode sequences may independently have the same or different lengths, such as at least 5, at least 10, at least 15, at least 20, at least 25, at least 30, at least 35, at least 40, at least 50 nucleotides in length. In some embodiments, the barcode sequence may be no more than 120, no more than 112, no more than 104, no more than 96, no more than 88, no more than 80, no more than 72, no more than 64, no more than 56, no more than 48, no more than 40, no more than 32, no more than 24, no more than 16, or no more than 8 nucleotides in length. Combinations of any of these are also possible, e.g., the barcode sequence may be between 5 and 10 nucleotides, between 8 and 15 nucleotides, etc.

The barcode sequence may be arbitrary or random. In certain cases, the barcode sequences are chosen so as to reduce or minimize homology with other components in a sample, e.g., such that the barcode sequences do not themselves bind to or hybridize with other nucleic acids suspected of being within the cell or other sample. In some embodiments, between a particular barcode sequence and another sequence (e.g., a cellular nucleic acid sequence in a sample or other barcode sequences in probes added to the sample), the homology may be less than 10%, less than 8%, less than 7%, less than 6%, less than 5%, less than 4%, less than 3%, less than 2%, or less than 1%. In some embodiments, the homology may be less than 20, 19, 18, 17, 16, 15, 14, 13, 12, 11, 10, 9, 8, 7, 6, 5, 4, 3, or 2 bases, and in some embodiments, the bases are consecutive bases.

In some embodiments, the number of distinct barcode sequences in a population of nucleic acid probes is less than the number of distinct targets (e.g., nucleic acid analytes and/or protein analytes) of the nucleic acid probes, and yet the distinct targets may still be uniquely identified from one another, e.g., by encoding a probe with a different combination of barcode sequences. However, not all possible combinations of a given set of barcode sequences need be used. For instance, each probe may contain 1, 2, 3, 4, 5, 6, 7, 8, 9, 10, 11, 12, 13, 14, 15, etc. or more barcode sequences. In some embodiments, a population of nucleic acid probes may each contain the same number of barcode sequences, although in other cases, there may be different numbers of barcode sequences present on the various probes.

As an illustrative example, a first probe may contain a first target-binding sequence, a first barcode sequence, and a second barcode sequence, while a second, different probe may contain a second target-binding sequence (that is different from the first target-binding sequence in the first probe), the same first barcode sequence as in the first probe, but a third barcode sequence instead of the second barcode sequence. Such probes may thereby be distinguished by determining the various barcode sequence combinations present or associated with a given probe at a given location in a sample.

In some embodiments, the nucleic acid probes disclosed herein may be made using only 2 or only 3 of the 4 bases, such as leaving out all the "G"s and/or leaving out all of the "C"s within the probe. Sequences lacking either "G"s or "C"s may form very little secondary structure, and can contribute to more uniform, faster hybridization in certain embodiments.

In some embodiments, a nucleic acid probe disclosed herein may contain a detectable label such as a fluorophore. In some embodiments, one or more probes of a plurality of nucleic acid probes used in an assay may lack a detectable label, while one or more other probes in the plurality each comprises a detectable label selected from a limited pool of distinct detectable labels (e.g., red, green, yellow, and blue fluorophores), and the absence of detectable label may be used as a separate "color." As such, detectable labels are not required in all cases. In some embodiments, a primary nucleic acid probe (e.g., a padlock probe) disclosed herein lacks a detectable label. While a detectable label may be incorporated into an amplification product of the primary nucleic acid probe, such as via incorporation of a modified nucleotide into an RCA product of a padlock probe, the amplification product in some embodiments is not detectably labeled. In some embodiments, a probe that binds to the primary nucleic acid probe or a product thereof (e.g., a secondary nucleic acid probe that binds to a barcode sequence or complement thereof in the primary nucleic acid probe or product thereof) comprises a detectable label and may be used to detect the primary nucleic acid probe or product thereof. In some embodiments, a secondary nucleic acid probe disclosed herein lacks a detectable label, and a detectably labeled probe that binds to the secondary nucleic acid probe or a product thereof (e.g., at a barcode sequence or complement thereof in the secondary nucleic acid probe or product thereof) can be used to detect the second nucleic acid probe or product thereof. In some embodiments, signals associated with the detectably labeled probes can be used to detect one or more barcode sequences in the secondary probe and/or one or more barcode sequences in the primary probe, e.g., by using sequential hybridization of detectably labeled probes, sequencing-by-ligation, and/or sequencing-by-hybridization. In some embodiments, the barcode sequences (e.g., in the secondary probe and/or in the primary probe) are used to combinatorially encode a plurality of analytes of interest. As such, signals associated with the detectably labeled probes at particular locations in a biological sample can be used to generate distinct signal signatures that each corresponds to an analyte in the sample, thereby identifying the analytes at the particular locations, e.g., for in situ spatial analysis of the sample.

In some embodiments, a nucleic acid probe herein comprises one or more other components, such as one or more primer binding sequences (e.g., to allow for enzymatic amplification of probes), enzyme recognition sequences (e.g., for endonuclease cleavage), or the like. The components of the nucleic acid probe may be arranged in any suitable order.

In some aspects, analytes are targeted by primary probes, which are barcoded through the incorporation of one or more barcode sequences (e.g., sequences that can be detected or otherwise "read") that are separate from a sequence in a primary probe that directly or indirectly binds the targeted analyte. In some aspects, the primary probes are in turn targeted by secondary probes, which are also barcoded through the incorporation of one or more barcode sequences that are separate from a recognition sequence in a secondary probe that directly or indirectly binds a primary probe or a product thereof. In some embodiments, a secondary probe may bind to a barcode sequence in the primary probe. In some embodiments, a secondary probe may bind to a complement of the barcode sequence in an RCA product of the primary probe. In some aspects, tertiary probes and optionally even higher order probes may be used to target the secondary probes, e.g., at a barcode sequence or complement thereof in a secondary probe or product thereof. In some embodiments, the tertiary probes and/or even higher order probes may comprise one or more barcode sequences and/or one or more detectable labels. In some embodiments, a tertiary probe is a detectably labeled probe that hybridizes to a barcode sequence (or complement thereof) of a secondary probe (or product thereof). In some embodiments, through the detection of signals associated with detectably labeled probes in a sample, the location of one or more analytes in the sample and the identity of the analyte(s) can be determined. In some embodiments, the presence/absence, absolute or relative abundance, an amount, a level, a concentration, an activity, and/or a relation with another analyte of a particular analyte can be analyzed in situ in the sample.

In some embodiments, provided herein are probes, probe sets, and assay methods to couple target nucleic acid detection, signal amplification (e.g., through nucleic acid amplification such as RCA, and/or hybridization of a plurality of detectably labeled probes, such as in hybridization chain reactions and the like), and decoding of the barcodes.

In some aspects, a primary probe, a secondary probe, and/or a higher order probe can be selected from the group consisting of a circular probe, a circularizable probe, and a linear probe. In some embodiments, a circular probe can be one that is pre-circularized prior to hybridization to a target nucleic acid and/or one or more other probes. In some embodiments, a circularizable probe can be one that can be circularized upon hybridization to a target nucleic acid and/or one or more other probes such as a splint. In some embodiments, a linear probe can be one that comprises a target recognition sequence and a sequence that does not hybridize to a target nucleic acid, such as a 5' overhang, a 3' overhang, and/or a linker or spacer (which may comprise a nucleic acid sequence or a non-nucleic acid moiety). In some embodiments, the sequence (e.g., the 5' overhang, 3' overhang, and/or linker or spacer) is non-hybridizing to the target nucleic acid but may hybridize to one another and/or one or more other probes, such as detectably labeled probes.

Specific probe designs can vary depending on the application. For instance, a primary probe, a secondary probe, and/or a higher order probe disclosed herein can comprise a padlock probe that does require gap filling to circularize upon hybridization to a template (e.g., a target nucleic acid and/or a probe such as a splint), a gapped padlock probe (e.g., one that require gap filling to circularize upon hybridization to a template), an L-shaped probe (e.g., one that comprises a target recognition sequence and a 5' or 3' overhang upon hybridization to a target nucleic acid or a probe), a U-shaped probe (e.g., one that comprises a target recognition sequence, a 5' overhang, and a 3' overhang upon hybridization to a target nucleic acid or a probe), a V-shaped probe (e.g., one that comprises at least two target recognition sequences and a linker or spacer between the target recognition sequences upon hybridization to a target nucleic acid or a probe), a probe or probe set for proximity ligation (such as those described in U.S. Pat. Nos. 7,914,987 and 8,580,504 incorporated herein by reference in their entireties, and probes for Proximity Ligation Assay (PLA) for the simultaneous detection and quantification of nucleic acid molecules and protein-protein interactions), or any suitable combination thereof. In some embodiments, a primary probe, a secondary probe, and/or a higher order probe disclosed herein can comprise a probe that is ligated to itself or another probe using DNA-templated and/or RNA-templated ligation. In some embodiments, a primary probe, a secondary probe, and/or a higher order probe disclosed herein can be a DNA molecule and can comprise one or more other types of nucleotides, modified nucleotides, and/or nucleotide analogues, such as one or more ribonucleotides. In some embodiments, the ligation can be a DNA ligation on a DNA template. In some embodiments, the ligation can be a DNA ligation on an RNA template, and the probes can comprise RNA-templated ligation probes. In some embodiments, a primary probe, a secondary probe, and/or a higher order probe disclosed herein can comprise a padlock-like probe or probe set. In some embodiments, a nucleic acid probe disclosed herein is part of a SNAIL (Splint Nucleotide Assisted Intramolecular Ligation) probe set, such as one described in US 2019/0055594 or US 2021/0164039 which are incorporated herein by reference in their entireties. In some embodiments, a nucleic acid probe disclosed herein is part of a PLAYR (Proximity Ligation Assay for RNA) probe set, such as one described in US 2016/0108458 which is incorporated herein by reference in its entirety. In some embodiments, a nucleic acid probe disclosed herein is part of a PLISH (Proximity Ligation in situ Hybridization) probe set, such as one described in US 2020/0224243 which is incorporated herein by reference in its entirety. Any suitable combination of the probe designs described herein can be used.

Any suitable circularizable probe or probe set, or indeed more generally circularizable reporter molecules, may be used to generate the RCA template which is used to generate the RCA product. For example, a circularizable probe or probe set may be used to generate a circular nucleic acid comprising a target hybridization region. The target hybridization region in the RCA product can comprise an identifying sequence, such as a sequence of a nucleic acid analyte or probe to which the circularizable probe or probe set hybridizes, or a barcode sequence. The circularizable probe or reporter (the RCA template) can be in the form of a linear molecule having ligatable ends which may circularized by ligating the ends together directly or indirectly, e.g. to each other, or to the respective ends of an intervening ("gap") oligonucleotide or to an extended 3' end of the circularizable RCA template. A circularizable template may also be provided in two or more parts, namely two or more molecules (e.g. oligonucleotides) which may be ligated together to form a circle. When said RCA template is circularizable it is circularized by ligation prior to RCA. Ligation may be templated using a ligation template, and in the case of padlock and molecular inversion probes and such like the target analyte may provide the ligation template, or it may be separately provided. The circularizable RCA template (or template part or portion) will comprise at its respective 3' and 5' ends regions of complementarity to corresponding cognate complementary regions (or binding sites) in the ligation template, which may be adjacent where the ends are directly ligated to each other, or non-adjacent, with an intervening "gap" sequence, where indirect ligation is to take place.

In the case of padlock probes, in one embodiment the ends of the padlock probe may be brought into proximity to each other by hybridization to adjacent sequences on a target nucleic acid molecule (such as a target analyte), which acts as a ligation template, thus allowing the ends to be ligated together to form a circular nucleic acid molecule, allowing the circularized padlock probe to act as a template for an RCA reaction. In such an example the terminal sequences of the padlock probe which hybridize to the target nucleic acid molecule will be specific to the target analyte in question, and will be replicated repeatedly in the RCA product. They may therefore act as a marker sequence indicative of that target analyte. Accordingly, it can be seen that the marker sequence in the RCA product may be equivalent to a sequence present in the target analyte itself. Alternatively, a marker sequence (e.g. tag or barcode sequence) may be provided in the non-target complementary parts of the padlock probe. In still a further embodiment, the marker sequence may be present in the gap oligonucleotide which is hybridized between the respective hybridized ends of the padlock probe, where they are hybridized to non-adjacent sequences in the target molecule. Such gap-filling padlock probes are akin to molecular inversion probes.

In some embodiments, similar circular RCA template molecules can be generated using molecular inversion probes. Like padlock probes, these are also typically linear nucleic acid molecules capable of hybridizing to a target nucleic acid molecule (such as a target analyte) and being circularized. The two ends of the molecular inversion probe may hybridize to the target nucleic acid molecule at sites which are proximate but not directly adjacent to each other, resulting in a gap between the two ends. The size of this gap may range from only a single nucleotide in some embodiments, to larger gaps of 100 to 500 nucleotides, or longer, in other embodiments. Accordingly, it is necessary to supply a polymerase and a source of nucleotides, or an additional gap-filling oligonucleotide, in order to fill the gap between the two ends of the molecular inversion probe, such that it can be circularized.

As with the padlock probe, the terminal sequences of the molecular inversion probe which hybridize to the target nucleic acid molecule, and the sequence between them, will be specific to the target analyte in question, and will be replicated repeatedly in the RCA product. They may therefore act as a marker sequence indicative of that target analyte. Alternatively, a marker sequence (e.g. tag or barcode sequence) may be provided in the non-target complementary parts of the molecular inversion probe.

In some embodiments, the probes disclosed herein may be invader probes, e.g., for generating a circular nucleic acid such as a circularized probe. Such probes are of particular utility in the detection of single nucleotide polymorphisms. The detection method of the present disclosure may, therefore, be used in the detection of a single nucleotide polymorphism, or indeed any variant base, in the target nucleic acid sequence. Probes for use in such a method may be designed such that the 3' ligatable end of the probe is complementary to and capable of hybridizing to the nucleotide in the target molecule which is of interest (the variant nucleotide), and the nucleotide at the 3' end of the 5' additional sequence at the 5' end of the probe or at the 5' end of another, different, probe part is complementary to the same said nucleotide, but is prevented from hybridizing thereto by a 3' ligatable end (e.g., it is a displaced nucleotide). Cleavage of the probe to remove the additional sequence provides a 5' ligatable end, which may be ligated to the 3' ligatable end of the probe or probe part if the 3' ligatable end is hybridized correctly to (e.g. is complementary to) the target nucleic acid molecule. Probes designed according to this principle provide a high degree of discrimination between different variants at the position of interest, as only probes in which the 3' ligatable end is complementary to the nucleotide at the position of interest may participate in a ligation reaction. In one embodiment, the probe is provided in a single part, and the 3' and 5' ligatable ends are provided by the same probe. In some embodiments, an invader probe is a padlock probe (an invader padlock or "iLock"), e.g., as described in Krzywkowski et al., *Nucleic Acids Research* 45, e161, 2017 and US 2020/0224244, which are incorporated herein by reference.

Other types of probe which result in circular molecules which can be detected by RCA and which comprise either a target analyte sequence or a complement thereof include selector-type probes described in US20190144940, which comprise sequences capable of directing the cleavage of a target nucleic acid molecule (e.g. a target analyte) so as to release a fragment comprising a target sequence from the target analyte and sequences capable of templating the circularization and ligation of the fragment. WO 2016/016452, which is incorporated herein by reference in its entirety, describes probes which comprise a 3' sequence capable of hybridizing to a target nucleic acid molecule (e.g. a target analyte) and acting as a primer for the production of a complement of a target sequence within the target nucleic acid molecule (e.g. by target templated extension of the primer), and an internal sequence capable of templating the circularization and ligation of the extended probe comprising the reverse complement of the target sequence within the target analyte and a portion of the probe. In the case of both such probes, target sequences or complements thereof are incorporated into a circularized molecule which acts as the template for the RCA reaction to generate the RCA product, which consequently comprises concatenated repeats of said target sequence. In some embodiments, said target sequence may act as, or may comprise a marker sequence within the RCA product indicative of the target analyte in question. Alternatively, a marker sequence (e.g. tag or barcode sequence) may be provided in the non-target complementary parts of the probes.

In some embodiments, a nucleic acid probe disclosed herein can be pre-assembled from multiple components, e.g., prior to contacting the nucleic acid probe with a target nucleic acid or a sample. In some embodiments, a nucleic acid probe disclosed herein can be assembled during and/or after contacting a target nucleic acid or a sample with multiple components. In some embodiments, a nucleic acid probe disclosed herein is assembled in situ in a sample. In some embodiments, the multiple components can be contacted with a target nucleic acid or a sample in any suitable order and any suitable combination. For instance, a first component and a second component can be contacted with a target nucleic acid, to allow binding between the components and/or binding between the first and/or second components with the target nucleic acid. Optionally a reaction involving either or both components and/or the target nucleic acid, between the components, and/or between either one or both components and the target nucleic acid can be performed, such as hybridization, ligation, primer extension and/or amplification, chemical or enzymatic cleavage, click chemistry, or any combination thereof. In some embodiments, a third component can be added prior to, during, or after the reaction. In some embodiments, a third component can be added prior to, during, or after contacting the sample with the first and/or second components. In some embodiments, the first, second, and third components can be contacted with the sample in any suitable combination, sequentially or simultaneously. In some embodiments, the nucleic acid probe can be assembled in situ in a stepwise manner, each step with the addition of one or more components, or in a dynamic process where all components are assembled together. One or more removing steps, e.g., by washing the sample such as under stringent conditions, may be performed at any point during the assembling process to remove or destabilize undesired intermediates and/or components at that point and increase the chance of accurate probe assembly and specific target binding of the assembled probe.

IV. Synchronized Rolling Circle Amplification In Situ

A. Rolling Circle Amplification (RCA)

In some embodiments, a probe disclosed herein is amplified through rolling circle amplification. In some embodiments, the primary probes, such as a padlock probe or a probe set that comprises a padlock probe, contain one or more barcodes. For example, the probe or probe set for amplification (e.g., as described in Section III) is a circular nucleic acid or is used to generate a circular nucleic acid comprising a target hybridization region and a hybridization region complementary to a polynucleotide. In some embodiments, the barcodes are bound by detection primary probes, which do not need to be fluorescent, but that include a target-binding portion (e.g., for hybridizing to one or more primary probes) and multiple other barcodes (e.g., secondary barcodes, versus the primary barcodes on the primary probes). In some embodiments, the barcodes of the detection primary probes are targeted by detectably labeled detection oligonucleotides, such as fluorescently labeled oligos. In some embodiments, one or more decoding schemes are used to decode the signals, such as fluorescence, for sequence determination. Exemplary decoding schemes are described in Eng et al., "Transcriptome-scale Super-Resolved Imaging in Tissues by RNA SeqFISH+," *Nature* 568(7751):235-239 (2019); Chen et al., "Spatially resolved, highly multiplexed RNA profiling in single cells," *Science;* 348(6233):aaa6090 (2015); U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, the method comprises using a circular or circularizable construct hybridized to the nucleic acid of interest to generate a circular nucleic acid. In some embodiments, the RCA comprises a linear RCA. In some embodiments, the RCA comprises a branched RCA. In some embodiments, the RCA comprises a dendritic RCA. In some embodiments, the RCA comprises any combination of the foregoing. In some embodiments, the circular nucleic acid is a construct formed using ligation. In some embodiments, the circular construct is formed using template primer extension followed by ligation. In some embodiments, the circular construct is formed by providing an insert between ends to be ligated. In some embodiments, the circular construct is formed using a combination of any of the foregoing. In some embodiments, the ligation is a DNA-DNA templated ligation. In some embodiments, the ligation is an RNA-RNA templated ligation. Exemplary RNA-templated ligation probes and methods are described in US 2020/0224244 which is incorporated herein by reference in its entirety. In some embodiments, the ligation is a RNA-DNA templated ligation. In some embodiments, a splint is provided as a template for ligation.

In some embodiments, a probe disclosed herein (e.g., a padlock probe) can comprise a 5' flap which may be recognized by a structure-specific cleavage enzyme, e.g. an enzyme capable of recognizing the junction between single-stranded 5' overhang and a DNA duplex, and cleaving the single-stranded overhang. It will be understood that the branched three-strand structure which is the substrate for the structure-specific cleavage enzyme may be formed by 5' end of one probe part and the 3' end of another probe part when both have hybridized to the target nucleic acid molecule, as well as by the 5' and 3' ends of a one-part probe. Enzymes suitable for such cleavage include Flap endonucleases (FENS), which are a class of enzymes having endonucleolytic activity and being capable of catalyzing the hydrolytic cleavage of the phosphodiester bond at the junction of single- and double-stranded DNA. Thus, in some embodiment, cleavage of the additional sequence 5' to the first target-specific binding site is performed by a structure-specific cleavage enzyme, e.g. a Flap endonuclease. Suitable Flap endonucleases are described in Ma et al. 2000. *JBC* 275, 24693-24700 and in US 2020/0224244, which are herein incorporated by reference in their entireties, and may include *P. furiosus* (Pfu), *A. fulgidus* (Afu), M jannaschii (Mja) or *M. thermoautotrophicum* (Mth). In other embodiments an enzyme capable of recognizing and degrading a single-stranded oligonucleotide having a free 5' end may be used to cleave an additional sequence (5' flap) from a structure as described above. Thus, an enzyme having 5' nuclease activity may be used to cleave a 5' additional sequence. Such 5' nuclease activity may be 5' exonuclease and/or 5' endonuclease activity. A 5' nuclease enzyme is capable of recognizing a free 5' end of a single-stranded oligonucleotide and degrading said single-stranded oligonucleotide. A 5' exonuclease degrades a single-stranded oligonucleotide having a free 5' end by degrading the oligonucleotide into constituent mononucleotides from its 5' end. A 5' endonuclease activity may cleave the 5' flap sequence internally at one or more nucleotides. Further, a 5' nuclease activity may take place by the enzyme traversing the single-stranded oligonucleotide to a region of duplex once it has recognized the free 5' end, and cleaving the single-stranded region into larger constituent nucleotides (e.g. dinucleotides or trinucleotides), or cleaving the entire 5' single-stranded region, e.g. as described in Lyamichev et al. 1999. *PNAS* 96, 6143-6148, which is incorporated by reference herein in its entirety, for Taq DNA polymerase and the 5' nuclease thereof. Preferred enzymes having 5' nuclease activity include Exonuclease VIII, or a native or recombinant DNA polymerase enzyme from *Thermus aquaticus* (Taq), *Thermus thermophilus* or *Thermus flavus*, or the nuclease domain therefrom.

Following formation of the circular nucleic acid, in some instances, an amplification primer is added. In other instances, the amplification primer is added with the primary and/or secondary probes. In some embodiments, the circular nucleic acid comprises a target hybridization region (e.g., for hybridizing to a nucleic acid analyte such as mRNA) and a hybridization region which is complementary to the polynucleotide (e.g., amplification primer) or a portion thereof. In some instances, the amplification primer may also be complementary to the target nucleic acid and the padlock probe (e.g., a SNAIL probe). In some embodiments, a washing step is performed to remove any unbound probes, primers, etc. In some embodiments, the wash is a stringency wash. Washing steps can be performed at any point during the process to remove non-specifically bound probes, probes that have ligated, etc.

In some instances, upon addition of a DNA polymerase in the presence of appropriate dNTP precursors and other cofactors, the amplification primer is elongated by replication of multiple copies of the template. The amplification step can utilize isothermal amplification or non-isothermal amplification. In some embodiments, after the formation of the hybridization complex and any subsequent circularization (such as ligation of, e.g., a padlock probe) the circular probe is rolling-circle amplified to generate a RCA product (e.g., amplicon) containing multiple copies of the circular.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

In some embodiments, rolling circle amplification products are generated using a polymerase selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof.

Following amplification, the sequence of the amplicon (e.g., RCA product) or a portion thereof, is determined or otherwise analyzed, for example by using detectably labeled probes and imaging. The sequencing or analysis of the amplification products can comprise sequencing by hybridization, sequencing by ligation, and/or fluorescent in situ sequencing, and/or wherein the in situ hybridization comprises sequential fluorescent in situ hybridization. In some instances, a sequence of the RCA product is detected using, e.g., the secondary and higher order probes and detection oligonucleotides described herein.

B. Compositions and Methods for Synchronizing RCA

Synchronization of RCA in situ may provide a number of advantages. For instance, synchronized RCA reactions (e.g., starting the reaction at the same time) of circularized probes targeting analytes at different locations in a tissue section may provide more homogeneously sized RCA products. In some aspects, synchronized RCA reactions may lead to signal spots (for RCA products) of homogeneous signal intensity and/or brightness. In some embodiments, the synchronization leads to less signal dim spots and/or more bright signal spots for the RCA products. In some embodiments, when RCA product size becomes more homogeneous, the amplification time can be decreased, which makes smaller RCA products of sufficient brightness to be detected. In some embodiments, as RCA product size and brightness become more homogeneous in the same microscope field of view, an RCA reaction time can be achieved so that there are few large signal spots (e.g., even for highly expressed genes) that would overlap with one another and/or mask adjacent smaller signal spots, thus ameliorating the issues of optical crowding and allowing neighbouring spots to better resolve from one another. In some embodiments, the RCA reaction time can be achieved such that there are few extremely bright signal spots that would render relatively dim spots to be detected simultaneously with the bright spots. In some aspects, synchronized RCA reactions may result at least 40%, at least 50%, at least 60%, at least 70%, or at least 80% of RCA products with signals when detected that are within 50% of the mean size and/or mean peak intensity. In some embodiments, the RCA reaction time can be achieved such that as many useful signal spots as possible can be detected and analyzed for accurately detecting and quantifying multiple analytes present in a biological sample (e.g., in situ). In some cases, by synchronizing the start of RCA in the biological sample, it may be easier to distinguish RCA signals from the background signals (e.g., noise).

In some aspects, provided herein is a method for analyzing a biological sample, comprising: contacting the biological sample with a binding mixture (e.g., a hybridization reaction mixture that allows the plurality of complexes to hybridize to the plurality of circular nucleic acids). In some embodiments, the biological sample comprises a plurality of circular nucleic acids each comprising a primer hybridization region, the binding mixture comprises a plurality of complexes each comprising a polymerase bound to a primer, wherein the primer comprises a sequence complementary to the primer hybridization region of one or more circular nucleic acids, and the polymerase activity of the polymerase is inhibited, thereby allowing the plurality of complexes to hybridize to the plurality of circular nucleic acids. In some embodiments, the method further comprises contacting the biological sample with a primer extension reaction mixture, e.g., an amplification reaction mixture for RCA. In some embodiments, the primer extension reaction mixture allows the polymerase to extend the primer hybridized to the primer hybridization region, thereby synchronizing rolling circle amplification the plurality of circular nucleic acids in the biological sample.

In some embodiments, provided herein is a method for analyzing a target nucleic acid in a biological sample, the method comprising: (a) contacting the biological sample with a circular probe or circularizable probe or probe set that hybridizes to the target nucleic acid; (b) contacting the biological sample with a binding mixture, wherein the binding mixture comprises a polymerase prebound to a polynucleotide comprising a sequence complementary to a hybridization region in the circular probe or circularized probe formed from the circularizable probe or probe set, and the activity of the polymerase is inhibited; and (c) contacting the biological sample with a primer extension reaction mixture to initiate polymerase activity, wherein a rolling circle amplification product of the circular or circularized probe is generated in the biological sample using the polynucleotide as a primer.

For example, as shown in FIG. 1A, a complex comprising a polymerase such as Phi29 and a primer can be preformed before the complex is contacted with a buffer (an OFF buffer for RCA) that stabilizes the complex but inhibits one or more activities of the polymerase, such as the polymerase and/or exonuclease activities. In some aspects, the preformed complex comprising a polymerase and a primer can be provided as a unit to the template for extension (e.g., circular nucleic acid in the biological sample). In some embodiments, the complexes are contacted with circular or circularized templates and RCA is then initiated at the same time by adding an RCA reaction buffer (an ON buffer for RCA) that lifts the inhibition on the polymerase and/or exonuclease activities of the enzyme. In some embodiments, a plurality of circular nucleic acids is bound to a plurality of target nucleic acids at various locations of the biological sample prior to rolling circle amplification.

In some aspects, provided herein is a method for analyzing a biological sample, comprising: contacting the biological sample with a binding mixture, wherein the biological sample comprises a plurality of circular nucleic acids each comprising a hybridization region hybridized to a polynucleotide, the binding mixture comprises a polymerase, and the polymerase activity of the polymerase is inhibited, thereby allowing the polymerase to bind to the plurality of circular nucleic acids; and contacting the biological sample with a primer extension reaction mixture to allow the polymerase to extend the polynucleotide hybridized to the hybridization region, thereby synchronizing rolling circle amplification of the plurality of circular nucleic acids in the biological sample.

In some embodiments, a complex comprising the polymerase, the circular nucleic acid, and a polynucleotide is formed in the biological sample. For example, the polynucleotide may comprise a sequence complementary to a portion of the circular nucleic acid. In some embodiments, the polynucleotide can comprise an exogenous primer added to the sample. For example, as shown in FIG. 1B, primers may be hybridized to circular or circularized probes at different locations in the sample, which is then contacted with a polymerase (e.g., Phi29) in an OFF buffer that inhibits the polymerase activity. The polymerase can diffuse in the sample and bind to the primers hybridized on the circular or circularized probes, but RCA is kept in check until unbound polymerases are removed and an ON buffer is applied to initiate RCA at the different locations. In these examples, the circular nucleic acids can comprise endogenous molecules in the biological sample, such as endogenous circular DNA or RNA molecules in a cell, e.g., mtDNA. Alternative, the circular nucleic acids can comprise products of endogenous molecules in the biological sample, such as circularized molecules generated from genomic DNA, cellular RNA such as mRNA, or circularized cDNA. In other cases, the circular nucleic acids can comprise probes targeting endogenous molecules in the biological sample, such as padlock probes targeting genomic DNA or cellular RNA such as mRNA. In other cases, the circular nucleic acids can comprise products of exogenous probes targeting endogenous molecules in the biological sample. In any of the preceding embodiments, the circular nucleic acids can be hybridized to one or more RCA products to generate additional RCA products using the circular nucleic acids as templates.

In some embodiments, the polynucleotide can comprise an endogenous molecule (e.g., a target nucleic acid) in the biological sample, such as genomic DNA or cellular RNA such as mRNA. In some embodiments, the polynucleotide can comprise cDNA. For example, as shown in FIG. 1C, a polymerase in an OFF buffer can be applied to a sample to bind to the 3' end of a polynucleotide (e.g., RNA or DNA, such as mRNA or cDNA) in the sample, and the polymerases loaded onto the polynucleotides can be activated with an ON buffer to use the polynucleotides as primers to prime synchronized RCA reactions using a circular or circularized probe as template. In some embodiments, the polynucleotide is an RNA such as mRNA, the circular or circularized probe hybridized to the RNA comprises DNA, and the RNA polynucleotide is used to prime the RCA reaction using the circular or circularized DNA template. In some embodiments, the polynucleotide can comprise a product of an endogenous molecule in the biological sample, such as a ligation, cleavage, or amplification product of genomic DNA or cellular RNA such as mRNA. In some embodiments, the polynucleotide can comprise a probe targeting an endogenous molecule in the biological sample, such as an L-shaped probe or a U-shaped probe. In these examples, the circular nucleic acid may hybridize to the polynucleotide which is used as a primer for RCA, for example, similar to the combined RCA-smFISH (RollFISH) approach described in Wu et al., *Commun Biol* 1: 209 (2018), which is incorporated herein by reference in its entirety. In some embodiments, the polynucleotide can comprise a product of an exogenous probe targeting an endogenous molecule in the biological sample. For instance, the polynucleotide itself can be an RCA product, and a circular or circularized probe can be hybridized to the RCA product to generate another RCA product using the circular or circularized probe as a template.

The binding mixture or OFF buffer can stabilize the polymerase and/or inhibit an activity of the polymerase, such as a polymerase activity and/or a nuclease activity. The binding mixture can comprise one or more deoxynucleoside triphosphates (dNTPs) and/or nucleoside triphosphates (NTPs). For instance, the binding mixture can comprise dATP, dTTP, dCTP, and/or dGTP. Alternatively, the binding mixture can be substantially free of dNTPs and/or NTPs. In some embodiments, the binding mixture can comprise a di-cation that is not a cofactor of the polymerase, such as $Ca^{2+}$ which can stabilize the polymerase without activating its polymerase activity and/or exonuclease activity.

In some embodiments, the binding mixture or OFF buffer or biological sample can be substantially free of a cofactor of the polymerase. A cofactor is a non-protein chemical compound or metallic ion that is required for an enzyme's activity as a catalyst. DNA and ribonucleic acid (RNA) polymerases in general require a divalent or trivalent metal cofactor cation to catalyze the polymerization of individual nucleotides into a polynucleotide. In some embodiments herein, the presence/absence of particular divalent cation(s) can be used to alter the kinetics of polymerases. Absent the metal cofactor in the proper oxidation state, polymerization will not occur at an appreciable rate even if all other necessary components are present. Metal cofactor cations may include $Co^{2+}$, $Mn^{2+}$, $Zn^{2+}$ and/or $Mg^{2+}$. Exemplary cofactor cations are disclosed in Vashishtha et al., *J Biol Chem* 291(40):20869-20875, 2016; US 2021/0047669; U.S. Pat. Nos. 5,409,811; 8,133,672; 8,658,365; and 9,279,155, all of which are herein incorporated by reference. The metal cofactors may be provided in the forms of salts such as $MgCl_2$ or $CoCl_2$. The salts form hydrates such as $MgCl_2 \cdot (H_2O)_x$ or $CoCl_2 \cdot nH_2O$ (n=1, 2, 6, and 9) in aqueous solution. One suitable metal cofactor is magnesium. Magnesium may be present as a magnesium salt such as magnesium chloride ($MgCl_2$). Magnesium may be provided as metallic magnesium, Mg(0), and can be oxidized by electrolysis at an anode in buffered solution to generate Mg(II). Another suitable metal cofactor is cobalt. Cobalt can be provided as a cobalt complex such as a cobalt (III) complex or a cobalt (I) complex. Example cobalt complexes include trans-Dichlorobis(ethylenediamine)cobalt(III) chloride, pentaaminechlorocobalt(III) chloride, hexamine cobalt(III) chloride, trans-dichlorotetrakis(imidazole)cobalt(III) chloride or chlorotris(triphenylphosphine)cobalt(I). The cobalt complex may be reduced or oxidized to cobalt(II) chloride ($CoCl_2$). For example, a Co(III)-complex can be reduced to a Co(II)-complex which can undergo ligand exchange with a buffered aqueous solution to form Co(II) which can then coordinate with a polymerase to activate it for polynucleotide synthesis. A ligand exchange reaction involves the substitution of one or more ligands in a complex ion with one or more different ligands.

Certain divalent or trivalent metal cofactors such as magnesium and manganese are known to interact with a polymerase to modulate the progress of the reaction. Such catalytic metal cofactors can coordinate with a polymerase and the triphosphate of a dNTP to catalyze the addition of a nucleotide to the 3' terminal nucleotide on the end of the initiator (e.g., a primer), creating a phosphodiester linkage between the nucleotide of the dNTP and the initiator and releases pyrophosphate (PPi). Other metal ions, such as $Ca^{2+}$, can interact with a polymerase, such as Phi29 or a variant or derivative thereof, to negative effect, e.g., to stabilize the enzyme and halt polymerization. Different metal co-factors can have varying catalytic effects upon the polymerization reaction depending upon the nature of the polymerization reaction, the polymerase used, the nucleotides employed, etc., and in some embodiments, the catalytic/non-catalytic effects of these cofactors are used to synchronize polymerization such as RCA reactions. For example, a first metal co-factor that interacts with a polymerase or polymerase-primer complex herein to support the polymerization reaction to a higher level than a second metal co-factor under the same conditions is termed a catalytic metal ion. In some aspects, such catalytic metals support the continued, iterative or processive polymerization of nucleic acids under the particular polymerase reaction conditions, e.g., through the addition on multiple bases, while in some cases, a given type of catalytic metal cofactor may only support addition of a single base. In some embodiments, catalytic metal cofactors, for example, for Phi29 or a variant or derivative thereof, may include $Co^{2+}$, $Mn^{2+}$, $Zn^{2+}$ or $Mg^{2+}$, or any combination thereof. In some embodiments, the binding mixture herein (e.g., in an OFF buffer) can be substantially free of $Co^{2+}$, $Mn^{2+}$, $Zn^{2+}$ and $Mg^{2+}$, so as to halt the polymerization such as RCA reactions while allowing a polymerase (or a polymerase-nucleic acid complex such as a polymerase-primer complex) to diffuse in a sample and bind to circular nucleic acids, primers, and/or complexes thereof.

In some embodiments, the binding mixture or OFF buffer or biological sample can comprise a chelating agent. For instance, the chelating agent can chelate a di-cation such as $Mg^{2+}$ from one or more prior reactions. As such, the chelating agent can chelate residual amounts of the di-cation in the biological sample, such as a tissue slice which has been contacted with a reaction mixture containing the di-cation (e.g., a ligation reaction mixture to circularize a padlock probe to form the circular nucleic acid). In some embodiments, the binding mixture can comprise EDTA, EGTA, BAPTA, DTPA, or a combination thereof. In some embodiments, one or more chelating agents in the binding mixture can chelate catalytic metal cofactors for Phi29 or a variant or derivative thereof, such as $Co^{2+}$, $Mn^{2+}$, $Zn^{2+}$ or $Mg^{2+}$, thereby sequestering these cofactors from polymerases in the reaction mixtures and/or in the sample in order to halt polymerization.

In some embodiments, the binding mixture or OFF buffer or biological sample can comprise one or more cofactors that interact with a polymerase, but that do not promote the polymerization reaction, and in some cases act to arrest or prevent polymerization and/or inhibit one or more other activities of the polymerase, such as the 3-5' exonuclease activity. In some embodiments, the binding mixture can comprise one or more non-catalytic metal ions, such as calcium, barium, strontium, iron, cobalt, nickel, tin, zinc, and europium. These metals can be added to the binding mixture and/or the sample in salt form such as $Sr(OAc)_2$, $Sr(OAc)_2$, $CoCl_2$, $SnCl_2$, $CaCl_2$, or $ZnSO_4$. A first metal co-factor that might be deemed to be catalytic under a first set of reaction conditions or relative to second metal co-factor, may be deemed to be a non-catalytic metal under another different set of reaction conditions, or with respect to a third metal co-factor. For instance, magnesium is generally known to support DNA polymerization. However, under certain conditions, and/or relative to manganese, magnesium can operate as a non-catalytic co-factor. In some embodiments herein, a catalytic co-factor supports polymerization to a greater degree than the non-catalytic metal under the same reaction conditions. In some embodiments, the relative catalytic impact is a function of the reactant turnover rate of the polymerization complex, with catalytic metal co-factors promoting a turnover that is at least two times, more preferably at least 5 times, still more preferably, at least 10 times, and in some cases 20 times, 50 times or more than that of the non-catalytic metal co-factor under the same reaction conditions. In some embodiments, the presence of a non-catalytic metal in the polymerase complex (e.g., in a binding mixture or an OFF buffer), through binding in or around the active site, results in the inability for the synthesis reaction to proceed out of the complexed state. In particular, the presence of calcium ions can modulate both the forward progress of the polymerase reaction, as well as the reverse progress of the reaction. As a result, in the presence of calcium or other non-catalytic metals, the complexed nucleotide is effectively sequestered in the polymerase complex. The reaction is an unproductive nucleotide binding event, that is, it is unable to proceed forward to incorporation, or in reverse to the release of the unincorporated nucleotide to yield a free polymerase.

In some embodiments, the catalytic metal is selected from $Mg^{2+}$, $Mn^{2+}$ and mixtures thereof, and the non-catalytic metal is selected from $Ca^{2+}$, $Zn^{2+}$, $CO^{2+}$, $Ni^{2+}$, $Eu^{2+}$, $Sr^{2+}$, $Ba^{2+}$, $Fe^{2+}$, $Eu^{2+}$ and mixtures thereof. In some embodiments, the binding mixture or OFF buffer comprises one or more of $Ca^{2+}$, $Zn^{2+}$, $Co^{2+}$, $Ni^{2+}$, $Eu^{2+}$, $Sr^{2+}$, $Ba^{2+}$, $Fe^{2+}$, and $Eu^{2+}$, and is substantially free of $Mg^{2+}$ and/or $Mn^{2+}$.

In some embodiments, the binding mixture or OFF buffer or biological sample can comprise one or more dNTPs. However, in some embodiments, due to the absence of one or more catalytic cofactors, the presence of one or more chelating agents for the catalytic cofactors, and/or the presence of one or more non-catalytic cofactors, the dNTPs are sequestered and the polymerase is unable to incorporate the dNTPs. In some embodiments, the binding mixture allows binding among a polymerase, a primer, and/or a circular nucleic acid, in order to form complexes at multiple locations in a sample that are ready to start RCA once the polymerase activity is turned on.

In some embodiments, the binding mixture or OFF buffer or biological sample can comprise one or more polynucleotides that can function as RCA primers. In some embodiments, since Phi29 possesses a 3'→5' exonuclease (proof-reading) activity acting preferentially on single-stranded DNA or RNA, in some embodiments, the polynucleotide (e.g., an exogenously added primer or a target nucleic acid in the sample) which functions as an RCA primer can be 3'-modified. In some embodiments, the polynucleotide can be 3' thiophosphate-protected, which protects the polynucleotide from 3'→5' exonuclease degradation by the polymerase while allowing priming by the polymerase. In some embodiments, the polynucleotide can comprise a 3'-tail of sufficient length in order to protect the sequence that functions as RCA primer from degradation by Phi29. In some embodiments, the 3'-end tail can be gradually digested until the remaining part can be converted to RCA primer and is extended along the circular template via the polymerase activity of Phi29. However, in some embodiments, due to the absence of one or more catalytic cofactors, the presence of one or more chelating agents for the catalytic cofactors, and/or the presence of one or more non-catalytic cofactors, the exonuclease activity of Phi29 may be effectively inhibited in the binding mixture or OFF buffer such that no 3' protective modification or 3'-tail is necessary. Thus, in some embodiments, the polynucleotide (e.g., an exogenously added primer or a target nucleic acid in the sample) can have a free 3' hydroxyl group available for nucleotide incorporation by Phi29.

In some embodiments, the binding mixture or OFF buffer or biological sample can comprise one or more polymerases. In some embodiments, the polymerase comprises a modified recombinant Phi29-type polymerase. In some embodiments, the polymerase comprises a modified recombinant Phi29, B103, GA-1, PZA, Phi15, BS32, M2Y, Nf, G1, Cp-1, PRD1, PZE, SF5, Cp-5, Cp-7, PR4, PR5, PR722, or L17 polymerase. In some embodiments, the polymerase comprises a modified recombinant DNA polymerase having at least one amino acid substitution or combination of substitutions as compared to a wildtype Phi29 polymerase. Exemplary polymerases are described in U.S. Pat. Nos. 8,257,954; 8,133,672; 8,343,746; 8,658,365; 8,921,086; and 9,279,155, all of which are herein incorporated by reference. In some embodiments, the polymerase is not directly or indirectly immobilized to a substrate, such as a bead or planar substrate (e.g., glass slide), prior to contacting a sample, although the sample may be immobilized on a substrate. In some embodiments, the polymerase is not attached to a nanopore, a nanopore membrane or an insulating support thereof. In some embodiments, the polymerase is diffusible in the binding mixture and/or in the biological sample. In some embodiments, a preformed complex comprising the polymerase and the RCA primer can be diffusible in the binding mixture and/or in the biological sample.

In some embodiments, the method can further comprise, between the contacting with the binding mixture and with the primer extension reaction mixture (e.g., amplification reaction mixture), a step of removing molecules of the polymerase and/or the polynucleotide that are not bound to the circular nucleic acid from the biological sample. In some embodiments, the method can further comprise one or more stringency washes between the contacting steps.

In some embodiments, the primer extension reaction mixture can comprise a deoxynucleoside triphosphate (dNTP) or derivative, variant, or analogue thereof. In some embodiments, the primer extension reaction mixture can comprise a catalytic cofactor of the polymerase. In any of the preceding embodiments, the primer extension reaction mixture can comprise a catalytic di-cation, such as $Mg^{2+}$ and/or $Mn^{2+}$. In some embodiments, the primer extension reaction mixture is substantially free of a non-catalytic cation, such as $Ca^{2+}$, $Zn^{2+}$, $Co^{2+}$, $Ni^{2+}$, $Eu^{2+}$, $Sr^{2+}$, $Ba^{2+}$, $Fe^{2+}$, $Eu^{2+}$ and mixtures thereof. In some embodiments, a catalytic cation in the primer extension reaction mixture can replace a non-catalytic cation in complex with the polymerase that is bound to the circular nucleic acid or the RCA primer, thus turning on the polymerase activity of the polymerase. In some embodiments, when the sample is contacted with a primer extension reaction mixture comprising a catalytic di-cation (such as $Mg^{2+}$ and/or $Mn^{2+}$), a non-catalytic cation (such as $Ca^{2+}$, $Zn^{2+}$, $CO^{2+}$, $Ni^{2+}$, $Eu^{2+}$, $Sr^{2+}$, $Ba^{2+}$, $Fe^{2+}$, and/or $Eu^{2+}$) bound to Phi29 is displaced, thereby activating the 5'→3' polymerase activity and the 3'→5' exonuclease (proofreading) activity of Phi29.

In some embodiments, the pH of the binding mixture and the primer extension reaction mixture can be substantially the same, e.g., about pH 8.5. In some embodiments, the pH of the binding mixture and the primer extension reaction mixture can be independently about 7.0, about 7.5, about 8.0, about 8.5, about 9.0, about 9.5, or about 10.0. In any of the preceding embodiments, the pH of the binding mixture and the primer extension reaction mixture can be independently about 8.1, about 8.2, about 8.3, about 8.4, about 8.5, about 8.6, about 8.7, about 8.8, about 8.9, or about 9.0.

In some embodiments, the primer extension reaction mixture can be substantially free of the polymerase and/or other polymerases. In some embodiments, molecules of the polymerase that are not bound to the circular nucleic acid and/or the RCA primer are removed from the biological sample. Thus, in some embodiments, substantially all of the polymerase molecules in the sample are bound to a circular nucleic acid and a RCA primer and ready to initiate RCA at the same time once the enzyme activity is turned on. The polynucleotides (e.g., exogenously added primers or target nucleic acids in the sample) hybridized to the hybridization region of the circular nucleic acids can be extended by the polymerase, thereby initiating rolling circle amplification simultaneously at different circular nucleic acids in a concerted manner. The RCA reactions can be terminated at the same time to provide a plurality of rolling circle amplification products.

In some embodiments, the plurality of rolling circle amplification products can have a mean, average, or medium diameter of about 0.05 µm, about 0.1 µm, about 0.2 µm, about 0.3 µm, about 0.4 µm, about 0.5 µm, about 0.6 µm, about 0.7 µm, about 0.8 µm, about 0.9 µm, about 1.0 µm, about 1.1 µm, about 1.2 µm, about 1.3 µm, about 1.4 µm, or about 1.5 µm, or between any of the aforementioned values. In some embodiments, the plurality of rolling circle amplification products can have a mean, average, or medium diameter smaller than 0.25 µm.

In some embodiments, the plurality of rolling circle amplification products can have a mean, average, or medium length of about 1 kb, about 2 kb, about 5 kb, about 10 kb, about 20 kb, about 30 kb, about 40 kb, about 50 kb, about 60 kb, or about 70 kb, or between any of the aforementioned values. In some embodiments, the plurality of rolling circle amplification products can have a mean, average, or medium length less than 20 kb or less than 10 kb.

In some embodiments, the mean, average, or medium number of copies of a unit sequence complementary to the circular nucleic acid in the plurality of rolling circle amplification products can be about 10, about 50, about 100, about 500, about 1,000, about 5,000, or about 10,000 or more.

In some embodiments, the mean, average, or medium number of copies of a unit sequence complementary to the circular nucleic acid in the plurality of rolling circle amplification products can be less than 100 or less than 1,000.

In some embodiments, the standard deviation of the diameter of the plurality of rolling circle amplification products is smaller than the standard deviation of the diameter of rolling circle amplification products generated using a non-synchronized method.

In some embodiments, the mean, average, or medium peak intensity value of the plurality of rolling circle amplification products can be between about 2 and about 10 times greater than a mean, average, or medium peak intensity value of rolling circle amplification products formed without synchronizing rolling circle amplification of the plurality of circular nucleic acids in the biological sample.

In some embodiments, the distribution of the relative observed signal of rolling circle amplification products formed with synchronizing rolling circle amplification of the plurality of circular nucleic acids in the biological sample may be narrower than the distribution of the relative observed signal of rolling circle amplification products formed without synchronizing rolling circle amplification of the plurality of circular nucleic acids in the biological sample.

In some embodiments, the synchronization leads to more homogeneously sized RCA products and/or brighter signal spots for the RCA products. In some embodiments, the synchronization leads to less dim signal spots and/or more bright signal spots for the RCA products. In some embodiments, when RCA product size becomes more homogeneous, the amplification time can be decreased, which makes smaller, but equally bright RCA products. In some embodiments, the polymerase extension may be performed for no more than 3 hours. In some embodiments, the polymerase extension may be performed for no more than 2 hours. In some embodiments, the polymerase extension may be performed for no more than 1 hours. In some embodiments, the polymerase extension may be performed for no more than 30 minutes. In any of the embodiments here, the polymerase extension, e.g., RCA, can be performed between about 20° C. and about 40° C., for instance, at about 25° C., about 26° C., about 27° C., about 28° C., about 29° C., about 30° C., about 31° C., about 32° C., about 33° C., about 34° C., about 35° C., about 36° C., or about 37° C., for less than about 5 minutes, less than about 10 minutes, less than about 15 minutes, less than about 20 minutes, less than about 25 minutes, less than about 30 minutes, less than about 35 minutes, less than about 40 minutes, less than about 45 minutes, less than about 50 minutes, less than about 55 minutes, less than about 60 minutes, less than about 65 minutes, less than about 70 minutes, less than about 75 minutes, less than about 80 minutes, less than about 85 minutes, less than about 90 minutes, less than about 95 minutes, less than about 100 minutes, less than about 105 minutes, less than about 110 minutes, less than about 115 minutes, less than about 120 minutes. In some embodiments, the polymerase extension can be performed for less than about 1 hour, less than about 2 hours, less than about 3 hours, less than about 4 hours, less than about 5 hours, less than about 6 hours, less than about 7 hours, less than about 8 hours, less than about 9 hours, less than about 10 hours, less than about 11 hours, less than about 12 hours, less than about 13 hours, less than about 14 hours, less than about 15 hours, less than about 16 hours, less than about 17 hours, less than about 18 hours, less than about 19 hours, less than about 20 hours, less than about 21 hours, less than about 22 hours, less than about 23 hours, less than about 24 hours, less than about 30 hours, less than about 35 hours, or less than about 40 hours. In a specific embodiment, the polymerase extension can be performed for between about 10 to 24 hours.

In some embodiments, using a method disclosed herein, RCA products of more homogeneous sizes (e.g., tighter distribution of sizes) are generated in a RCA time of less than about 30 minutes. For example, FIG. 4C shows representative images after feature detection and filtering in the control and synchronized groups with 30 minutes of RCA. The synchronized group showed a trend of improved detection of RCA products at the locations where the target gene expression is expected in the brain tissue. Thus, compared to non-synchronized in situ RCA reactions, the synchronization can facilitate the better detection and/or resolving of more RCA products.

V. Signal Amplification, Detection and Analysis

In some aspects, the provided methods involve analyzing, e.g., detecting or determining, one or more sequences present in the circular nucleic acids and/or polynucleotides and/or in a product or derivative thereof, such as in an amplified padlock probe. In some cases, the analysis is performed on one or more images captured, and may comprise processing the image(s) and/or quantifying signals observed. For example, the analysis may comprise processing information of one or more cell types, one or more types of biomarkers, a number or level of a biomarker, and/or a number or level of cells detected in a particular region of the sample. In some embodiments, the analysis comprises detecting a sequence e.g., a barcode present in the sample. In some embodiments, the analysis includes quantification of puncta (e.g., if amplification products are detected). In some cases, the analysis includes determining whether particular cells and/or signals are present that correlate with one or more biomarkers from a particular panel. In some embodiments, the obtained information may be compared to a positive and negative control, or to a threshold of a feature to determine if the sample exhibits a certain feature or phenotype. In some cases, the information may comprise signals from a cell, a region, and/or comprise readouts from multiple detectable labels. In some case, the analysis further includes displaying the information from the analysis or detection step. In some embodiments, software may be used to automate the processing, analysis, and/or display of data.

In some embodiments, a method disclosed herein may also comprise one or more signal amplification components. In some embodiments, the present disclosure relates to the detection of nucleic acids sequences in situ using probe hybridization and generation of amplified signals associated with the probes, wherein background signal is reduced and sensitivity is increased. In some embodiments, the RCA product generated from synchronized RCA can be detected in with a method that comprises signal amplification.

Exemplary signal amplification methods include targeted deposition of detectable reactive molecules around the site of probe hybridization, targeted assembly of branched structures (e.g., bDNA or branched assay using locked nucleic acid (LNA)), programmed in situ growth of concatemers by enzymatic rolling circle amplification (RCA) (e.g., as described in US 2019/0055594 incorporated herein by reference), hybridization chain reaction, assembly of topologically catenated DNA structures using serial rounds of chemical ligation (clampFISH), signal amplification via hairpin-mediated concatemerization (e.g., as described in US 2020/0362398 incorporated herein by reference), e.g., primer exchange reactions such as signal amplification by exchange reaction (SABER) or SABER with DNA-Exchange (Exchange-SABER). In some embodiments, a non-enzymatic signal amplification method may be used.

The detectable reactive molecules may comprise tyramide, such as used in tyramide signal amplification (TSA) or multiplexed catalyzed reporter deposition (CARD)-FISH. In some embodiments, the detectable reactive molecule may be releasable and/or cleavable from a detectable label such as a fluorophore. In some embodiments, a method disclosed herein comprises multiplexed analysis of a biological sample comprising consecutive cycles of probe hybridization, fluorescence imaging, and signal removal, where the signal removal comprises removing the fluorophore from a fluorophore-labeled reactive molecule (e.g., tyramide). Exemplary detectable reactive reagents and methods are described in U.S. Pat. No. 6,828,109, US 2019/0376956, WO 2019/236841, WO 2020/102094, WO 2020/163397, and WO 2021/067475, all of which are incorporated herein by reference in their entireties.

In some embodiments, hybridization chain reaction (HCR) can be used for signal amplification. HCR is an enzyme-free nucleic acid amplification based on a triggered chain of hybridization of nucleic acid molecules starting from HCR monomers, which hybridize to one another to form a nicked nucleic acid polymer. This polymer is the product of the HCR reaction which is ultimately detected in order to indicate the presence of the target analyte. HCR is described in detail in Dirks and Pierce, 2004, PNAS, 101 (43), 15275-15278 and in U.S. Pat. Nos. 7,632,641 and 7,721,721 (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401), all of which are incorporated by reference in their entireties. HCR monomers typically comprise a hairpin, or other metastable nucleic acid structure. In the simplest form of HCR, two different types of stable hairpin monomer, referred to here as first and second HCR monomers, undergo a chain reaction of hybridization events to form a long nicked double-stranded DNA molecule when an "initiator" nucleic acid molecule is introduced. The HCR monomers have a hairpin structure comprising a double stranded stem region, a loop region connecting the two strands of the stem region, and a single stranded region at one end of the double stranded stem region. The single stranded region which is exposed (and which is thus available for hybridization to another molecule, e.g. initiator or other HCR monomer) when the monomers are in the hairpin structure may be known as the "toehold region" (or "input domain"). The first HCR monomers each further comprise a sequence which is complementary to a sequence in the exposed toehold region of the second HCR monomers. This sequence of complementarity in the first HCR monomers may be known as the "interacting region" (or "output domain"). Similarly, the second HCR monomers each comprise an interacting region (output domain), e.g. a sequence which is complementary to the exposed toehold region (input domain) of the first HCR monomers. In the absence of the HCR initiator, these interacting regions are protected by the secondary structure (e.g. they are not exposed), and thus the hairpin monomers are stable or kinetically trapped (also referred to as "metastable"), and remain as monomers (e.g. preventing the system from rapidly equilibrating), because the first and second sets of HCR monomers cannot hybridize to each other. However, once the initiator is introduced, it is able to hybridize to the exposed toehold region of a first HCR monomer, and invade it, causing it to open up. This exposes the interacting region of the first HCR monomer (e.g. the sequence of complementarity to the toehold region of the second HCR monomers), allowing it to hybridize to and invade a second HCR monomer at the toehold region. This hybridization and invasion in turn opens up the second HCR monomer, exposing its interacting region (which is complementary to the toehold region of the first HCR monomers), and allowing it to hybridize to and invade another first HCR monomer. The reaction continues in this manner until all of the HCR monomers are exhausted (e.g. all of the HCR monomers are incorporated into a polymeric chain). Ultimately, this chain reaction leads to the formation of a nicked chain of alternating units of the first and second monomer species. The presence of the HCR initiator is thus required in order to trigger the HCR reaction by hybridization to and invasion of a first HCR monomer. The first and second HCR monomers are designed to hybridize to one another are thus may be defined as cognate to one another. They are also cognate to a given HCR initiator sequence. HCR monomers which interact with one another (hybridize) may be described as a set of HCR monomers or an HCR monomer, or hairpin, system.

An HCR reaction could be carried out with more than two species or types of HCR monomers. For example, a system involving three HCR monomers could be used. In such a system, each first HCR monomer may comprise an interacting region which binds to the toehold region of a second HCR monomer; each second HCR monomer may comprise an interacting region which binds to the toehold region of a third HCR monomer; and each third HCR monomer may comprise an interacting region which binds to the toehold region of a first HCR monomer. The HCR polymerization reaction would then proceed as described above, except that the resulting product would be a polymer having a repeating unit of first, second and third monomers consecutively. Corresponding systems with larger numbers of sets of HCR monomers could readily be conceived. Branching HCR systems have also been devised and described (see, e.g., WO 2020/123742 incorporated herein by reference), and may be used in the methods herein.

In some embodiments, similar to HCR reactions that use hairpin monomers, linear oligo hybridization chain reaction (LO-HCR) can also be used for signal amplification. In some embodiments, provided herein is a method of detecting an analyte in a sample comprising: (i) performing a linear oligo hybridization chain reaction (LO-HCR), wherein an initiator is contacted with a plurality of LO-HCR monomers of at least a first and a second species to generate a polymeric LO-HCR product hybridized to a target nucleic acid molecule, wherein the first species comprises a first hybridization region complementary to the initiator and a second hybridization region complementary to the second species, wherein the first species and the second species are linear, single-stranded nucleic acid molecules; wherein the initiator is provided in one or more parts, and hybridizes directly or indirectly to or is comprised in the target nucleic acid molecule; and (ii) detecting the polymeric product, thereby detecting the analyte. In some embodiments, the first species and/or the second species may not comprise a hairpin structure. In some embodiments, the plurality of LO-HCR monomers may not comprise a metastable secondary structure. In some embodiments, the LO-HCR polymer may not comprise a branched structure. In some embodiments, performing the linear oligo hybridization chain reaction comprises contacting the target nucleic acid molecule with the initiator to provide the initiator hybridized to the target nucleic acid molecule. In any of the embodiments herein, the target nucleic acid molecule and/or the analyte can be an RCA product. Exemplary methods and compositions for LO-HCR are described in US 2021/0198723, incorporated herein by reference in its entirety.

In some embodiments, detection of nucleic acids sequences in situ includes combination of synchronized RCA with an assembly for branched signal amplification. In some embodiments, the assembly complex comprises an amplifier hybridized directly or indirectly (via one or more oligonucleotides) to a sequence of the RCA product. In some embodiments, the assembly includes one or more amplifiers each including an amplifier repeating sequence. In some aspects, the one or more amplifiers is labeled. Described herein is a method of using the aforementioned assembly, including for example, using the assembly in multiplexed error-robust fluorescent in situ hybridization (MERFISH) applications, with branched DNA amplification for signal readout. In some embodiments, the amplifier repeating sequence is about 5-30 nucleotides, and is repeated N times in the amplifier. In some embodiments, the amplifier repeating sequence is about 20 nucleotides, and is repeated at least two times in the amplifier. In some aspects, the one or more amplifier repeating sequence is labeled. For exemplary branched signal amplification, see e.g., U.S. Pat. Pub. No. US20200399689A1 and Xia et al., Multiplexed Detection of RNA using MERFISH and branched DNA amplification. Scientific Reports (2019), each of which is fully incorporated by reference herein.

In some embodiments, the RCA product can be detected in with a method that comprises signal amplification by performing a primer exchange reaction (PER). In various embodiments, a primer with domain on its 3' end binds to a catalytic hairpin, and is extended with a new domain by a strand displacing polymerase. For example, a primer with domain 1 on its 3' ends binds to a catalytic hairpin, and is extended with a new domain 1 by a strand displacing polymerase, with repeated cycles generating a concatemer of repeated domain 1 sequences. In various embodiments, the strand displacing polymerase is Bst. In various embodiments, the catalytic hairpin includes a stopper which releases the strand displacing polymerase. In various embodiments, branch migration displaces the extended primer, which can then dissociate. In various embodiments, the primer undergoes repeated cycles to form a concatemer primer. In various embodiments, a plurality of concatemer primers is contacted with a sample comprising RCA products generated using methods described herein. In various embodiments, the RCA product may be contacted with a plurality of concatemer primers and a plurality of labeled probes. see e.g., U.S. Pat. Pub. No. US20190106733, which is incorporated herein by reference, for exemplary molecules and PER reaction components.

In some embodiments, the RCA product can be detected by providing detection probes, such as probes for performing a chain reaction that forms an amplification product, e.g., HCR. In some embodiments, the analysis comprises determining the sequence of all or a portion of the amplification product. In some embodiments, the analysis comprises detecting a sequence present in the amplification product. In some embodiments, the sequence of all or a portion of the amplification product is indicative of the identity of a region of interest in a target nucleic acid. In other embodiments, the provided methods involve analyzing, e.g., detecting or determining, one or more sequences present in the polynucleotide probes (e.g., a barcode sequence present in an overhang region of the first and/or second probe).

In some embodiments, the methods comprise sequencing all or a portion of the amplification product, such as one or more barcode sequences present in the amplification product. In some embodiments, the analysis and/or sequence determination comprises sequencing all or a portion of the amplification product or the probe(s) and/or in situ hybridization to the amplification product or the probe(s). In some embodiments, the sequencing step involves sequencing by hybridization, sequencing by ligation, and/or fluorescent in situ sequencing, hybridization-based in situ sequencing and/or wherein the in situ hybridization comprises sequential fluorescent in situ hybridization. In some embodiments, the analysis and/or sequence determination comprises detecting a polymer generated by a hybridization chain reaction (HCR) reaction, see e.g., US 2017/0009278, which is incorporated herein by reference, for exemplary probes and HCR reaction components. In some embodiments, the detection or determination comprises hybridizing to the amplification product a detection oligonucleotide labeled with a fluorophore, an isotope, a mass tag, or a combination thereof. In some embodiments, the detection or determination comprises imaging the amplification product. In some embodiments, the target nucleic acid is an mRNA in a tissue sample, and the detection or determination is performed when the target nucleic acid and/or the amplification product is in situ in the tissue sample.

In some aspects, the provided methods comprise imaging the amplification product (e.g., amplicon) and/or one or more portions of the polynucleotides, for example, via binding of the detection probe and detecting the detectable label. In some embodiments, the detection probe comprises a detectable label that can be measured and quantitated. The terms "label" and "detectable label" comprise a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

The term "fluorophore" comprises a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (MaxVision Biosciences), and/or a very intense black dye (e.g., Sudan Black, or comparable dark chromophore).

In some embodiments, a detectable probe containing a detectable label can be used to detect one or more polynucleotide(s) and/or amplification products (e.g., amplicon) described herein. In some embodiments, the methods involve incubating the detectable probe containing the detectable label with the sample, washing unbound detectable probe, and detecting the label, e.g., by imaging.

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}$I, $^{35}$S, $^{14}$C, or $^{3}$H. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519, which are herein incorporated by reference in their entireties. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes). Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264, all of which are herein incorporated by reference in their entireties. As used herein, the term "fluorescent label" comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-!2-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.). Custom synthesis of nucleotides having other fluorophores can be found in Henegariu et al. (2000) Nature Biotechnol. 18:345, which is herein incorporated by reference in its entirety).

Other fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62, which is herein incorporated by reference in its entirety).

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. In some embodiments, an antibody refers to an antibody molecule of any class, or any sub-fragment thereof, such as a Fab.

Other suitable labels for a polynucleotide sequence may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleotide and/or an polynucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, and PCT publication WO 1991/017160, all of which are herein incorporated by reference in their entireties. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

In some aspects, the detecting involves using detection methods such as flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy. In some aspects, the flow cytometry is mass cytometry or fluorescence-activated flow cytometry. In some aspects, the detecting comprises performing microscopy, scanning mass spectrometry or other imaging techniques described herein. In such aspects, the detecting comprises determining a signal, e.g., a fluorescent signal.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (e.g., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECS™), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequencing can be performed in situ. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (e.g., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014) *Science,* 343(6177), 1360-1363, which are incorporated by reference in their entirety. In addition, examples of methods and systems for performing in situ sequencing are described in US 2016/0024555, US 2019/0194709, and in U.S. Pat. Nos. 10,138,509, 10,494,662 and 10,179,932, all of which are herein incorporated by reference in their entireties. Exemplary techniques for in situ sequencing comprise, but are not limited to, STARmap (described for example in Wang et al., (2018) *Science,* 361(6499) 5691), MERFISH (described for example in Moffitt, (2016) *Methods in Enzymology,* 572, 1-49), hybridization-based in situ sequencing (HybISS) (described for example in Gyllborg et al., Nucleic Acids Res (2020) 48(19):e112, and FISSEQ (described for example in US 2019/0032121), all of which are herein incorporated by reference in their entireties.

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/005986, US 2005/0100900, U.S. Pat. No. 9,217,178, US 2009/0118128, US 2012/0270305, US 2013/0260372, and US 2013/0079232, all of which are herein incorporated by reference in their entireties.

In some embodiments, sequence analysis of nucleic acids (e.g., nucleic acids such as probes or RCA products comprising barcode sequences generated using the circular nucleic acid as template) can be performed by sequential hybridization (e.g., sequencing by hybridization and/or sequential in situ fluorescence hybridization). Sequential fluorescence hybridization can involve sequential hybridization of detectable probes comprising an oligonucleotide and a detectable label. In some embodiments, a method disclosed herein comprises sequential hybridization of the detectable probes disclosed herein, including detectably labeled probes (e.g., fluorophore conjugated oligonucleotides) and/or probes that are not detectably labeled per se but are capable of binding (e.g., via nucleic acid hybridization) and being detected by detectably labeled probes. Exemplary methods comprising sequential fluorescence hybridization of detectable probes are described in US 2019/0161796, US 2020/0224244, US 2022/0010358, US 2021/0340618, and WO 2021/138676, all of which are incorporated herein by reference. In some embodiments, the methods provided herein can include analyzing the identifier sequences (e.g., analyte sequences or barcode sequences) by sequential hybridization and detection with a plurality of labeled probes (e.g., detection oligonucleotides).

In some embodiments, sequence detection comprises contacting the biological sample with one or more intermediate probes that directly or indirectly hybridize to the rolling circle amplification product, wherein the one or more intermediate probes are detectable using one or more detectably-labeled probes, and dehybridizing the one or more intermediate probes and/or the one or more detectably-labeled probes from the rolling circle amplification product. In some embodiments, the one or more intermediate probes comprise one or more overhang regions (e.g., a 5' and/or 3' end of the probe that does not hybridize to the rolling circle amplification product). A probe comprising a single overhang region may be referred to as an "L-shaped probe," and a probe comprising two overhangs may be referred to as a "U-shaped probe." In some cases, the overhang region comprises a binding region for binding one or more detectably-labeled probes. In some embodiments, the detecting comprises contacting the biological sample with a pool of intermediate probes corresponding to different barcode sequences or portions thereof, and a pool of detectably-labeled probes corresponding to different detectable labels. In some embodiments, the biological sample is sequentially contacted with different pools of intermediate probes. In some instances, a common or universal pool of detectably-labeled probes is used in a plurality of sequential hybridization steps (e.g., with different pools of intermediate probes).

In some embodiments, provided herein are methods for in situ analysis of analytes in a sample using sequential probe hybridization. In some aspects provided herein is a method for analyzing a biological sample, comprising: a) generating a rolling circle amplification product (RCP) of a circular probe described herein, the RCP comprising an identifier sequence such as a barcode sequence or analyte sequence, wherein the identifier sequence is associated with an analyte of interest and is assigned a signal code sequence; b) contacting the biological sample with a first probe (e.g., an intermediate probe such as an L-probe) and a first detectably labeled probe to generate a first complex comprising the first probe hybridized to the RCP and the first detectably labeled probe hybridized to the first probe, wherein the first probe comprises (i) a recognition sequence (e.g., a target-binding sequence) complementary to the identifier sequence (e.g., barcode sequence or analyte sequence) and (ii) a first landing sequence (e.g., an overhang sequence), and wherein the first detectably labeled probe comprises a sequence complementary to the first landing sequence; c) detecting a first signal associated with the first detectably labeled probe, wherein the first signal corresponds to a first signal code in the signal code sequence; d) contacting the biological sample with a second probe (e.g., an intermediate probe such as L-probe) and a second detectably labeled probe to generate a second complex comprising the second probe hybridized to the RCP and the second detectably labeled probe hybridized to the second probe, wherein the second probe comprises (i) a recognition sequence (e.g., a target-binding sequence) complementary to the identifier sequence (e.g., barcode sequence or analyte sequence) and (ii) a second landing sequence (e.g., an overhang sequence), and wherein the second detectably labeled probe comprises a sequence complementary to the second landing sequence; and e) detecting a second signal associated with the second detectably labeled probe, wherein the second signal corresponds to a second signal code in the signal code sequence, wherein the signal code sequence comprising the first signal code and the second signal code is determined at a location in the biological sample, thereby decoding the identifier sequence (e.g., barcode sequence or analyte sequence) and identifying the analyte of interest at the location in the biological sample. In some embodiments, the detectable label of the first detectably labeled probe and the detectable label of the second detectably labeled probe are the same. In some embodiments, the detectable labels of the first detectably labeled probe and the second detectably labeled probe are different. In some embodiments, the first signal code and the second signal code are the same. In some embodiments, the first signal code and the second signal code are different.

In some embodiments, the first probe (e.g., a first intermediate probe such as a first L-probe), the second probe (e.g., a second intermediate probe such as a second L-probe), and one or more subsequent probes (e.g., subsequent intermediate probe such as subsequent L-probes) are contacted with the biological sample sequentially in a predetermined sequence which corresponds to the signal code sequence assigned to the identifier sequence (e.g., barcode sequence or analyte sequence), wherein the one or more subsequent probes each comprises (i) a recognition sequence complementary to the identifier sequence (e.g., barcode sequence or analyte sequence) and (ii) an overhang sequence complementary to a detectably labeled probe of a pool (e.g., a universal pool across different cycles of probe hybridization) of detectably labeled probes. In some embodiments, the biological sample is contacted with the first probe before the second probe and one or more subsequent probes. In some embodiments, the biological sample is contacted with the second after the first probe and before and one or more subsequent probes. In some embodiments, the biological sample is contacted with the one or more subsequent probes after the first probe. In some embodiments, the biological sample is contacted with the one or more subsequent probes after the first probe and the second probe.

In some embodiments, the first detectably labeled probe and the second detectably labeled probe are in the pool of detectably labeled probes. A pool of detectably labeled probes may comprises at least two detectably labeled probes, and may be used for multiplexing analyses of two or more target analytes (e.g., target nucleic acids) in a biological sample. In some embodiments, the contacting in b) comprises contacting the biological sample with the universal pool of detectably labeled probes, and the contacting in d) comprises contacting the biological sample with the universal pool of detectably labeled probes. In some embodiments, the universal pool of detectably labeled probes used in the contacting in b) is the same as the universal pool of detectably labeled probes used in the contacting in d). In some embodiments, the universal pool comprises detectably labeled probes each having a detectable label corresponding to a different nucleic acid sequence for hybridization to a landing sequence (e.g., an overhang sequence) in a probe (e.g., an intermediate probe such as an L-probe). In some embodiments, the number of different detectably labeled probes in the universal pool is four.

In some embodiments, the one or more subsequent probes are contacted with the biological sample to determine signal codes in the signal code sequence until sufficient signal codes have been determined to decode the identifier sequence (e.g., barcode sequence or analyte sequence), thereby identifying the target analyte (e.g., target nucleic acid). In some embodiments, the method further comprises a step of removing the first probe and/or the first detectably labeled probe from the biological sample before contacting the sample with a subsequent probe and a detectably labeled probe hybridizing to the subsequent probe. In some embodiments, the method further comprises a step of removing the second probe and/or the second detectably labeled probe from the biological sample, before contacting the sample with a subsequent probe and a detectably labeled probe hybridizing to the subsequent probe.

In some embodiments, the method further comprises identifying multiple different target analytes present at locations (e.g., different locations) in the biological sample. In some embodiments, each different target analyte is assigned a different signal code sequence and is targeted by a circular or circularizable probe or probe set comprising a complement of a different barcode sequence of the plurality of barcode sequences. In some embodiments, the number of different probes (e.g., L-probes that have different recognition sequences that bind to the barcode sequences) in each pool of probes is greater than the number of different detectably labeled probes in the universal pool of detectably labeled probes. In some embodiments, the number of different detectably labeled probes in the universal pool is four. In some embodiments, the number of different probes in each pool of probes (e.g., L-probes) is about 10, about 20, about 30, about 40, about 50, about 100, about 200, about 500, about 1,000, or more. In some embodiments, the number of different recognition sequences (e.g., recognition sequences that bind to the barcode sequences) of probes in each pool of probes in at least about 10, such as at least any of about 20, 30, 40, 50, 100, 200, 500, 1,000, or more.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309: 1728-1732, and in U.S. Pat. Nos. 5,599,675; 5,750,341; 6,969,488; 6,172,218; and 6,306,597, all of which are herein incorporated by reference in their entireties.

In some embodiments, the barcodes of the probes (e.g., the padlock probe or the first and/or second probe) are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed (e.g., detected or sequenced) using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," *Nature* 568(7751):235-239 (2019); Chen et al., "Spatially resolved, highly multiplexed RNA profiling in single cells," *Science;* 348(6233):aaa6090 (2015); Gyllborg et al., Nucleic Acids Res (2020) 48(19):e112; U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004), which are herein incorporated by reference in their entirety.

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181, which are herein incorporated by reference in their entirety.

VI. Kits

Also provided herein are kits, for example comprising one or more probes (e.g., circular nucleic acids) and polynucleotides, e.g., any described in Section III, and reagents for performing the methods provided herein, for example reagents required for one or more steps comprising hybridization, ligation, amplification, detection, sequencing, and/or sample preparation as described herein. In some embodiments, the kit further comprises a target nucleic acid, e.g., any described in Section III. In some embodiments, any or all of the probes and/or polynucleotides are DNA molecules. In some embodiments, the target nucleic acid is a messenger RNA molecule. In some embodiments, the kit further comprises a ligase, for instance for forming a circular probe from the padlock probe. In some embodiments, the ligase has DNA-splinted DNA ligase activity. In some embodiments, the ligase has RNA-splinted ligase activity. In some embodiments, the kit further comprises a polymerase, for instance for performing amplification of the padlock probe, e.g., using any of the methods described in Section V. In some embodiments, the kit further comprises a primer for amplification.

In some embodiments, disclosed herein is a kit for analyzing a biological sample, comprising: (i) a binding mixture comprising a plurality of complexes each comprising a polymerase bound to a primer, and a chelating agent, wherein the binding mixture is substantially free of deoxynucleoside triphosphates (dNTPs); and (ii) a primer extension reaction mixture comprising dNTPs and a di-cation, wherein the primer extension reaction mixture is substantially free of the polymerase. In any of the preceding embodiments, the primers in the plurality of complexes may be the same. Alternatively, in any of the preceding embodiments, the primers in two or more of the plurality of complexes can be different. In any of the preceding embodiments, the polymerase can be Phi29 DNA polymerase and the di-cation can be $Mg^{2+}$, $Co^{2+}$, and/or $Mn^{2+}$.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, modified nucleotides, reagents for additional assays.

VII. Applications

In some aspects, the provided embodiments can be applied in an in situ method of analyzing nucleic acid sequences, such as an in situ transcriptomic analysis or in situ sequencing, for example from intact tissues or samples in which the spatial information has been preserved. In some aspects, the embodiments can be applied in an imaging or detection method for multiplexed nucleic acid analysis. In some aspects, the provided embodiments can be used to identify or detect regions of interest in target nucleic acids.

In some embodiments, the region of interest comprises a single-nucleotide polymorphism (SNP). In some embodiments, the region of interest comprises is a single-nucleotide variant (SNV). In some embodiments, the region of interest comprises a single-nucleotide substitution. In some embodiments, the region of interest comprises a point mutation. In some embodiments, the region of interest comprises a single-nucleotide insertion.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples.

In some aspects, the embodiments can be applied to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, or in personalized medicine or ancestry.

VIII. Terminology

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample and/or a probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Non-native bases that can be included in a nucleic acid or nucleotide may be utilized.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (e.g., can be oligoribonucleotides) and/or deoxyribonucleotide monomers (e.g., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vi) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(vii) Primer Extension

Two nucleic acid sequences can become linked (e.g., hybridized) by an overlap of their respective terminal complementary nucleic acid sequences (e.g., 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(viii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(ix) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'→3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(x) Antibody

An "antibody" is a polypeptide molecule that recognizes and binds to a complementary target antigen. Antibodies typically have a molecular structure shape that resembles a Y shape. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form antigen binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site.

Antibodies can also refer to an "epitope binding fragment" or "antibody fragment," which as used herein, generally refers to a portion of a complete antibody capable of binding the same epitope as the complete antibody, albeit not necessarily to the same extent. Although multiple types of epitope binding fragments are possible, an epitope binding fragment typically comprises at least one pair of heavy and light chain variable regions (VH and VL, respectively) held together (e.g., by disulfide bonds) to preserve the antigen binding site, and does not contain all or a portion of the Fc region. Epitope binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an epitope binding fragment comprises an F(ab')$_2$ fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide.

(xi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a probe for in situ assay or analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a probe associated with a feature. For example, detectably labelled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, probe, or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™ Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18 (5)), DIDS, DiI (DilC18(3)), DiO (DiOC18(3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and—methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

EXAMPLES

The following examples are included for illustrative purposes only and are not intended to limit the scope of the present disclosure.

Example 1: Synchronizing In Situ Rolling Circle Amplification (RCA)

This example discloses exemplary methods that improve in situ target detection and image analysis. Certain known methods of in situ signal amplification using RCA can yield amplification products of heterogeneous intensity and size, where RCA products of weak intensity and/or small size may not reach a threshold of detection. In contrast, RCA products of disproportionately strong intensity and/or large size may result in optical overcrowding, especially when in close proximity. In both cases, sensitivity can be compromised, reducing the quality of image analysis. The methods in this example can facilitate production of homogeneous amplification products, providing solutions to a previously unmet need for improved target analysis.

Improved target detection and image analysis can be achieved by synchronizing the initiation of in situ RCA, thereby providing RCA products having homogeneous intensities and sizes generated in concerted reactions at multiple locations in a sample. Complexing primers with a polymerase (e.g., Phi29) before addition to a sample containing a circular template (e.g., circular nucleic acid comprising a hybridization region to the primer) can lead to synchronicity, as demonstrated in the following experiments.

Glutamate Decarboxylase 2 (Gad2)

A sample of fresh/frozen mouse brain was prepared for in situ analysis of glutamate decarboxylase 2 (Gad2) gene expression. Padlock probes for Gad2 were added to the sample and allowed to hybridize. Following probe hybridization, the sample was washed to remove unbound probes. For padlock probe ligation, T4 RNA ligase 2 (T4 Rnl2) and RNase inhibitors were added to the sample and incubated. Experimental and control groups were set up as shown in Table 1 below.

TABLE 1

| Mix | Component | Primer+ | Phi29+ | Complex | Control |
| --- | --- | --- | --- | --- | --- |
| Ligation Mix | Primer | − | + | − | + |
| Binding Buffer | Primer | + | − | + | Not Applicable |
|  | Phi29 | − | + | + | Not Applicable |
| Reaction Mix | Phi29 | + | − | − | + |

In the "Complex" group, a complex of Phi29 and the primer was preformed by mixing the two together in a binding buffer. EDTA in the binding buffer ("OFF buffer") can chelate $Mg^{2+}$ in the sample which may be present in residual amount from one or more earlier reactions, such as padlock ligation that used a buffer containing $Mg^{2+}$. Since $Mg^{2+}$ is a cofactor of Phi29, the binding buffer can inhibit polymerase activity. The reaction mixture containing the preformed Phi29-primer complex was then added to the tissue sample and incubated for 50 minutes at 37° C. This incubation allowed the Phi29-primer complexes to diffuse through the sample and "find" circularized padlock probes hybridized to the target nucleic acids of interest, e.g., in this example Gad2 mRNA molecules in the sample. Unbound complexes were removed by washing three times. Then, the remaining Phi29-primer complexes in the sample were contacted with a reaction buffer (pH 8.5) containing $Mg^{2+}$, dNTPs, and Tris-HCl. The inhibition of the Phi29 polymerase activity was lifted and RCA was allowed to proceed for 3 hours at 37° C. before washing the tissue with TE buffer.

For comparison, similar experiments were performed with either Phi29 alone ("Phi29+") or the primer ("Primer+") alone in the binding buffer (Table 1). In the "Primer+" group, Phi29 was provided in the amplification reaction buffer ("Reaction Mix" in Table 1), whereas the primer was provided in the binding buffer. In the "Phi29+" group, the primer was provided in the ligation reaction mix ("Ligation Mix" in Table 1), whereas Phi29 was provided in the binding buffer. Note in the "Complex" group, Phi29 and the primer were pre-complexed in the binding buffer; there was no primer in the ligation mix and no Phi29 in the amplification reaction buffer. In the "Control" group, the primer was provided in the ligation mix, Phi29 was provided in the amplification reaction buffer, and the sample was incubated with the amplification reaction buffer ("Reaction Mix") and stopped after 3 hours of incubation with TE buffer. Sample processing, probe hybridization, ligation, and RCA in the experimental and control groups were carried out essentially as described above. All experiments were performed in duplicate.

Prior to imaging, tissue samples were treated with Gold Antifade Mountant medium to optimize the light path and prolong sample integrity. Imaging was carried out at 40× magnification, with a 4×4 field-of-view (FOV) for each section, using an Orca Fusion camera.

Figure 2A:
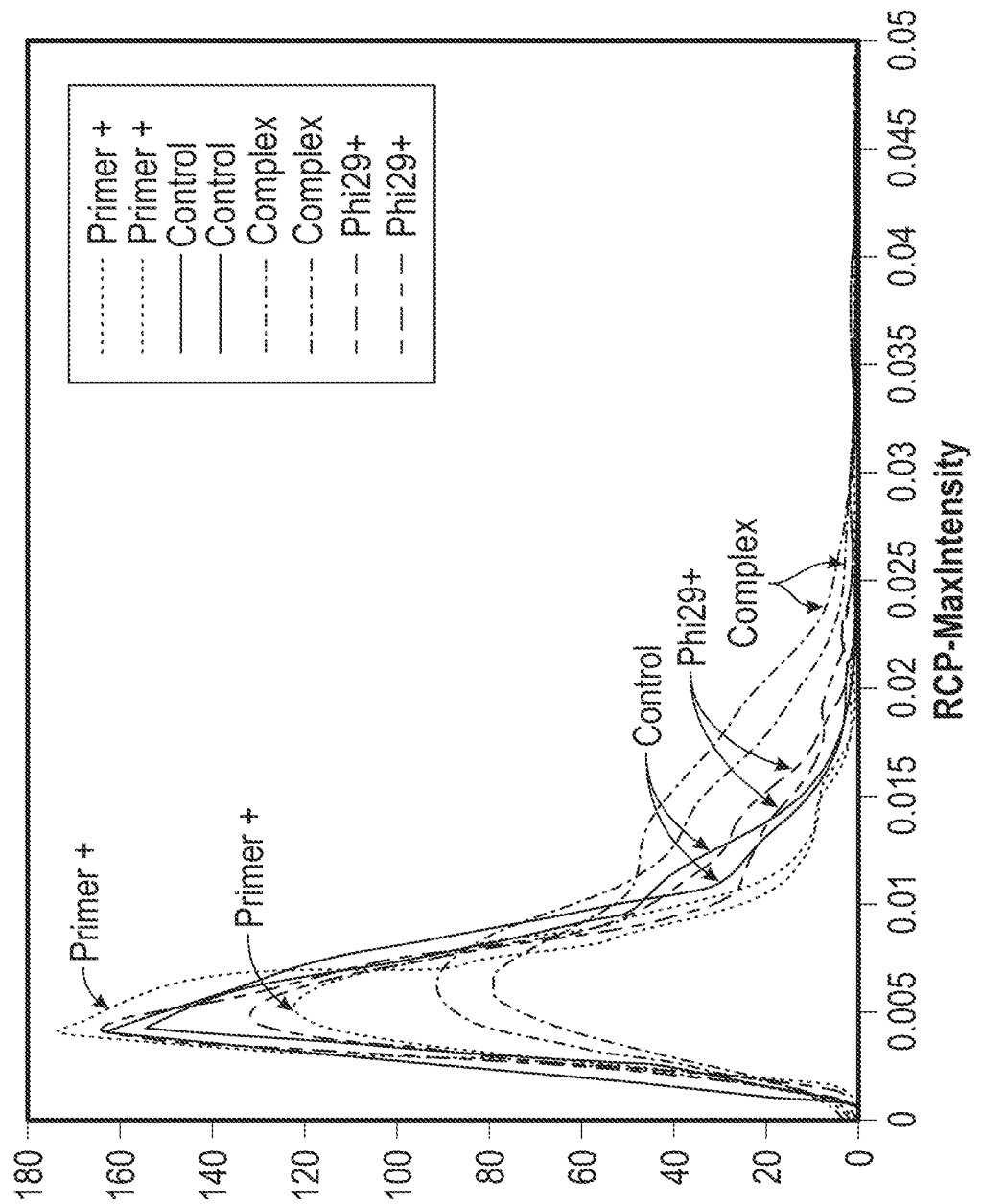
FIGS. 2A-2B show results in feature intensity (FIG. 2A) and estimated feature size (FIG. 2B) in exemplary methods for detecting Gad2 using a Phi29-primer complex in an OFF buffer ("Complex") to synchronize RCA, as compared to methods using Phi29 alone in the OFF buffer ("Phi29+"), primer alone in the OFF buffer ("Primer+"), and an unsynchronized control protocol ("Control").
Figure 2B:
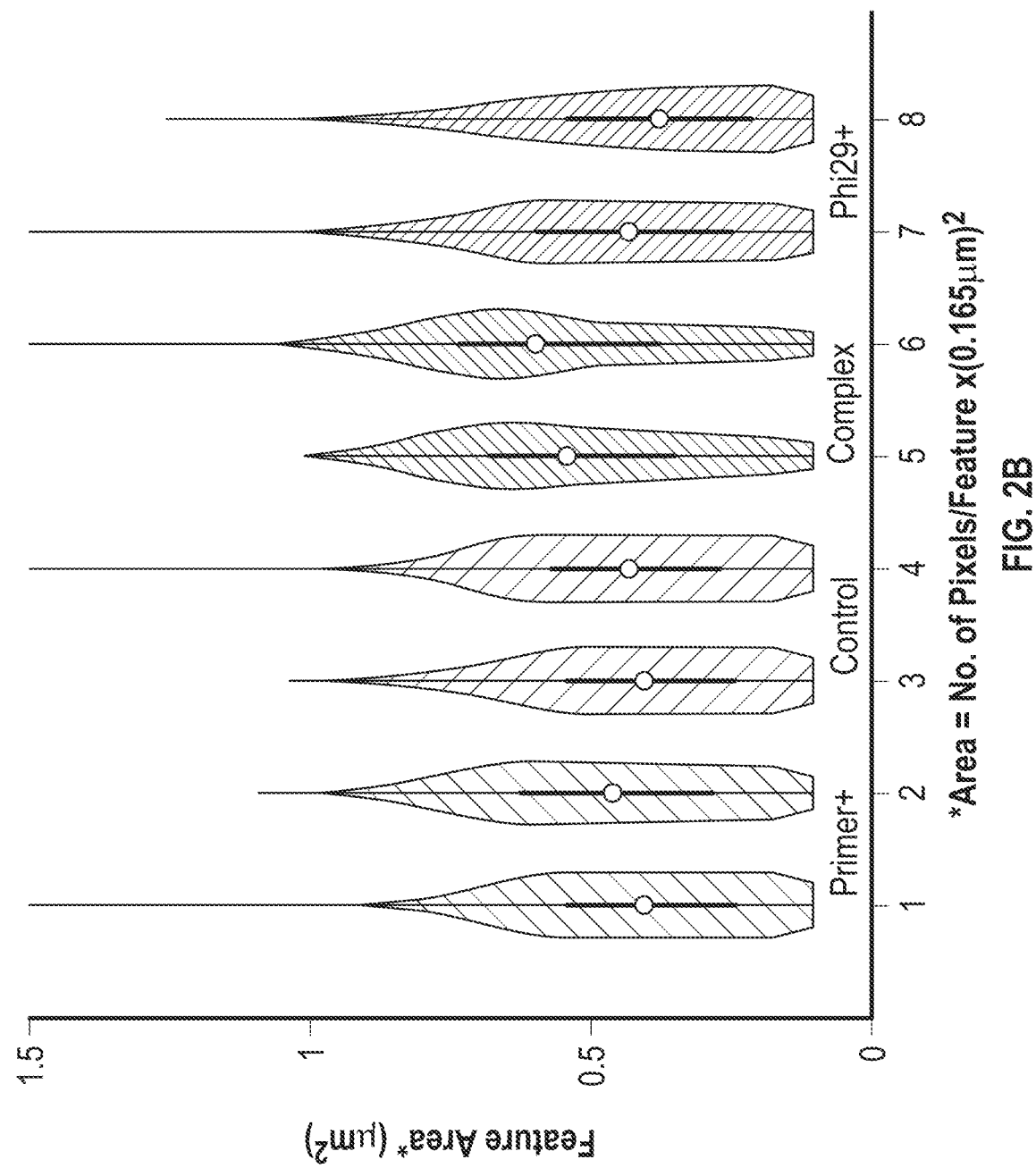

FIGS. 2A-2B show results in feature intensity (FIG. 2A) and estimated feature size (FIG. 2B) between experiments with the Phi29-primer complex in the OFF buffer and experiments with Phi29 alone in the OFF buffer, primer alone in the OFF buffer, and the control group. FIG. 2A shows a trend of the intensity of features detected in the "Complex" group being greater than feature intensity detected in the other groups. FIG. 2B shows a trend toward narrower feature area ($\mu m^2$) distribution in the "Complex" group as compared to the other groups. Therefore, a trend of larger spot size as well as narrower spot size distribution was observed in the "Complex" group using synchronized RCA reactions. The control group showed higher number of RCA products per pixel area, likely because the longer incubation time with Phi29 present in the sample led to the generation of more RCA products.

Taken together, these results indicate that complexing of polymerase and primers prior to contacting the sample may affect feature characteristics by enhancing RCA product intensity and reducing heterogeneity in feature size distribution.

Vesicular Glutamate Transporter 1 (Slc17a7)

To further assess the impact of synchronizing amplification on feature characteristics, another set of experiments was performed with vesicular glutamate transporter 1 (Slc17a7) as the target of interest essentially as described above for Gad2. In the Slc17a7 experiments, the Phi29-primer complex in the OFF buffer was incubated with the tissue sample for 120 minutes at 37° C. Imaging was performed essentially as described above.

Figure 3A:
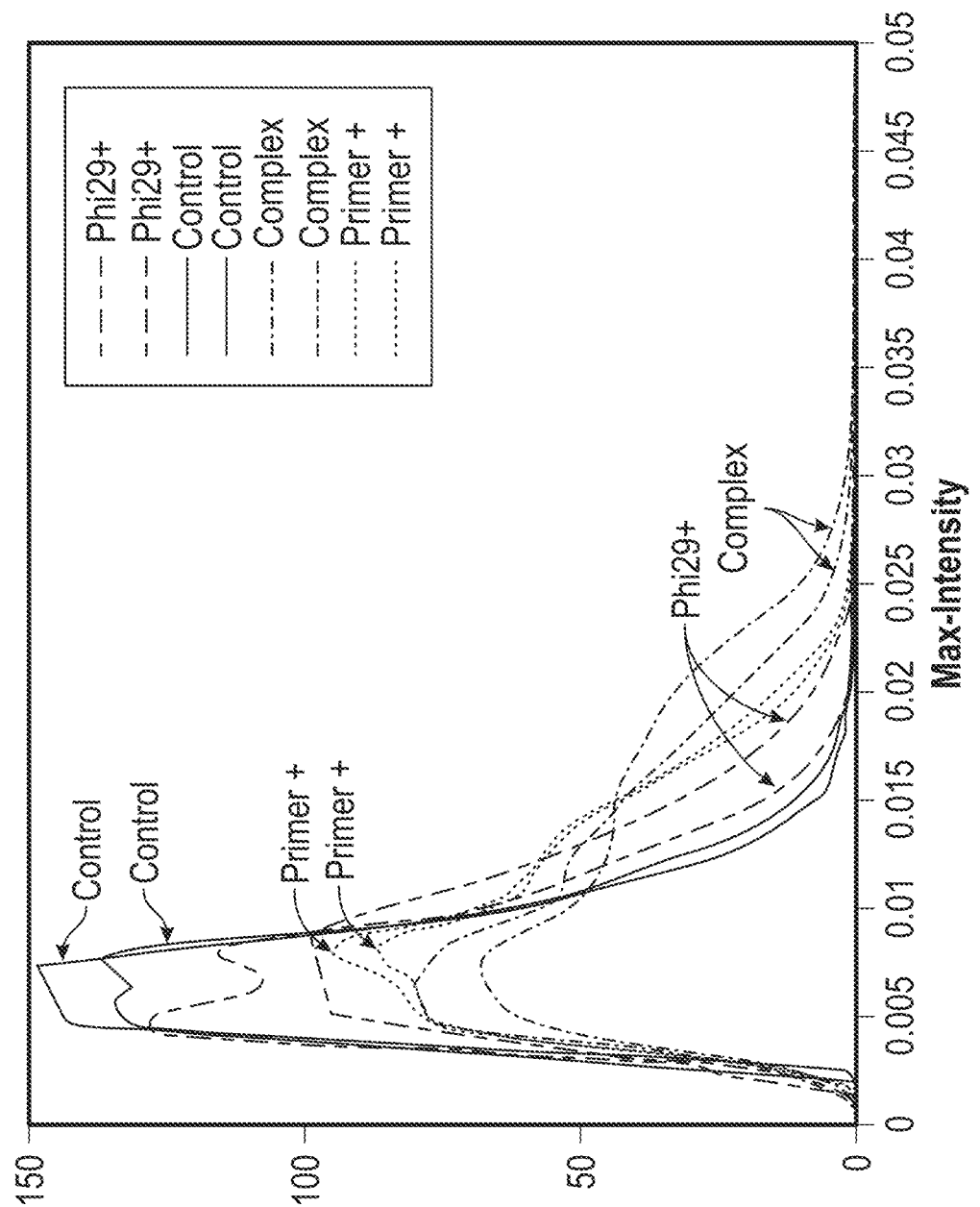
FIGS. 3A-3B show results in feature intensity (FIG. 3A) and estimated feature size distribution (FIG. 3B) in exemplary methods for detecting Slc17a7 using a Phi29-primer complex in an OFF buffer ("Complex") to synchronize RCA, as compared to methods using Phi29 alone in the OFF buffer ("Phi29+"), primer alone in the OFF buffer ("Primer+"), and an unsynchronized control protocol.
Figure 3B:
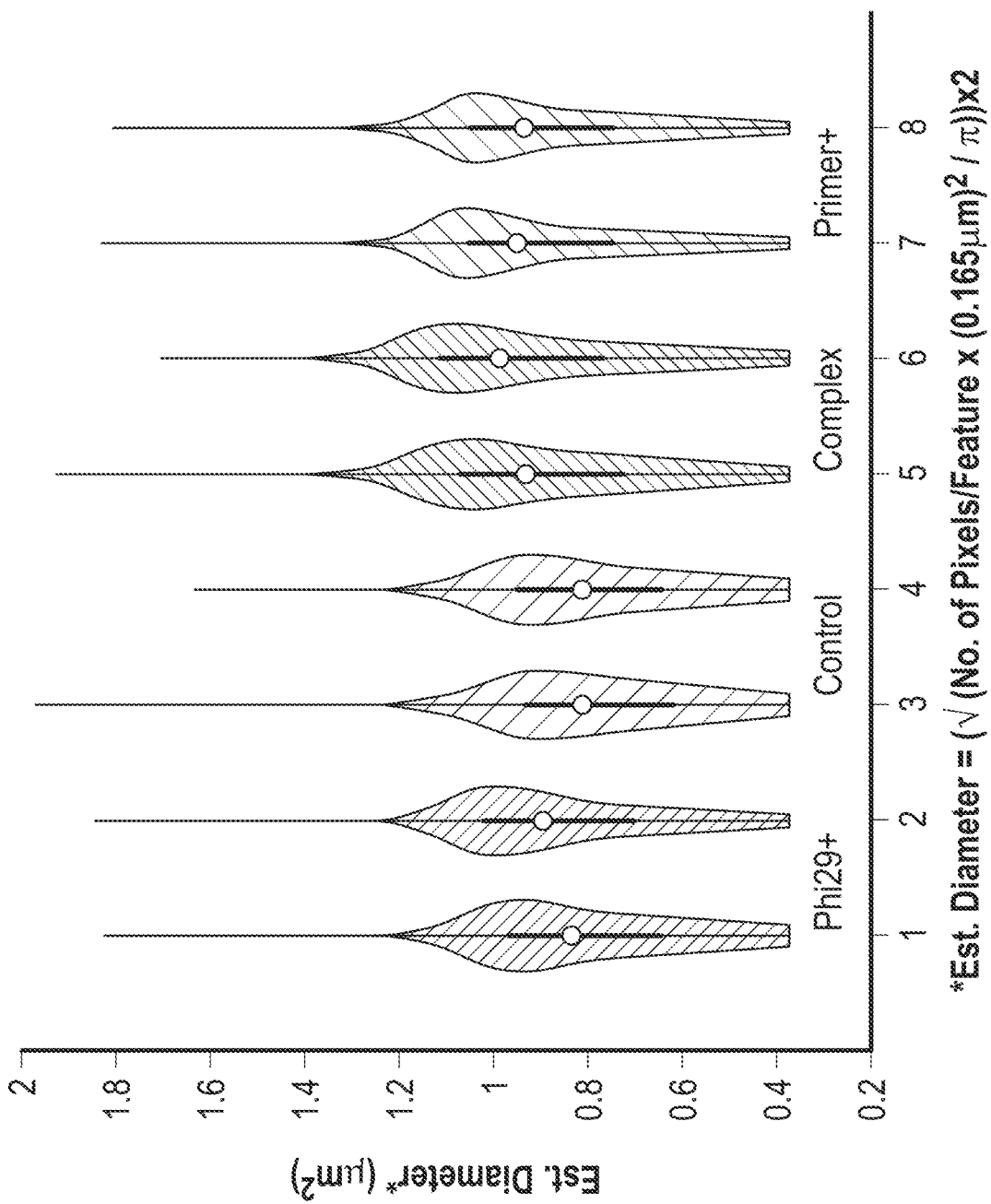

FIGS. 3A-3B show the feature intensity and apparent size, respectively, among experimental and control groups. FIG. 3A shows a trend of increased feature intensity in the "Complex" group relative to the other groups. FIG. 3B shows a trend toward narrower feature area ($\mu m^2$) distribution in the "Complex" group as compared to the control group. Together, these results are consistent with those observed for Gad2. Application of preformed Phi29-primer complexes to synchronize RCA appears to lead to increased spot intensity and a tighter size distribution of RCA products detected in the sample.

Time course experiments were conducted to probe the effects of synchronizing amplification by complexing polymerase (Phi29) and primers, using Slc17a7 as a target. RCA was allowed to proceed for 60 minutes and 120 minutes to test the effects on feature characteristics by increasing amplification times.

Figure 4A:
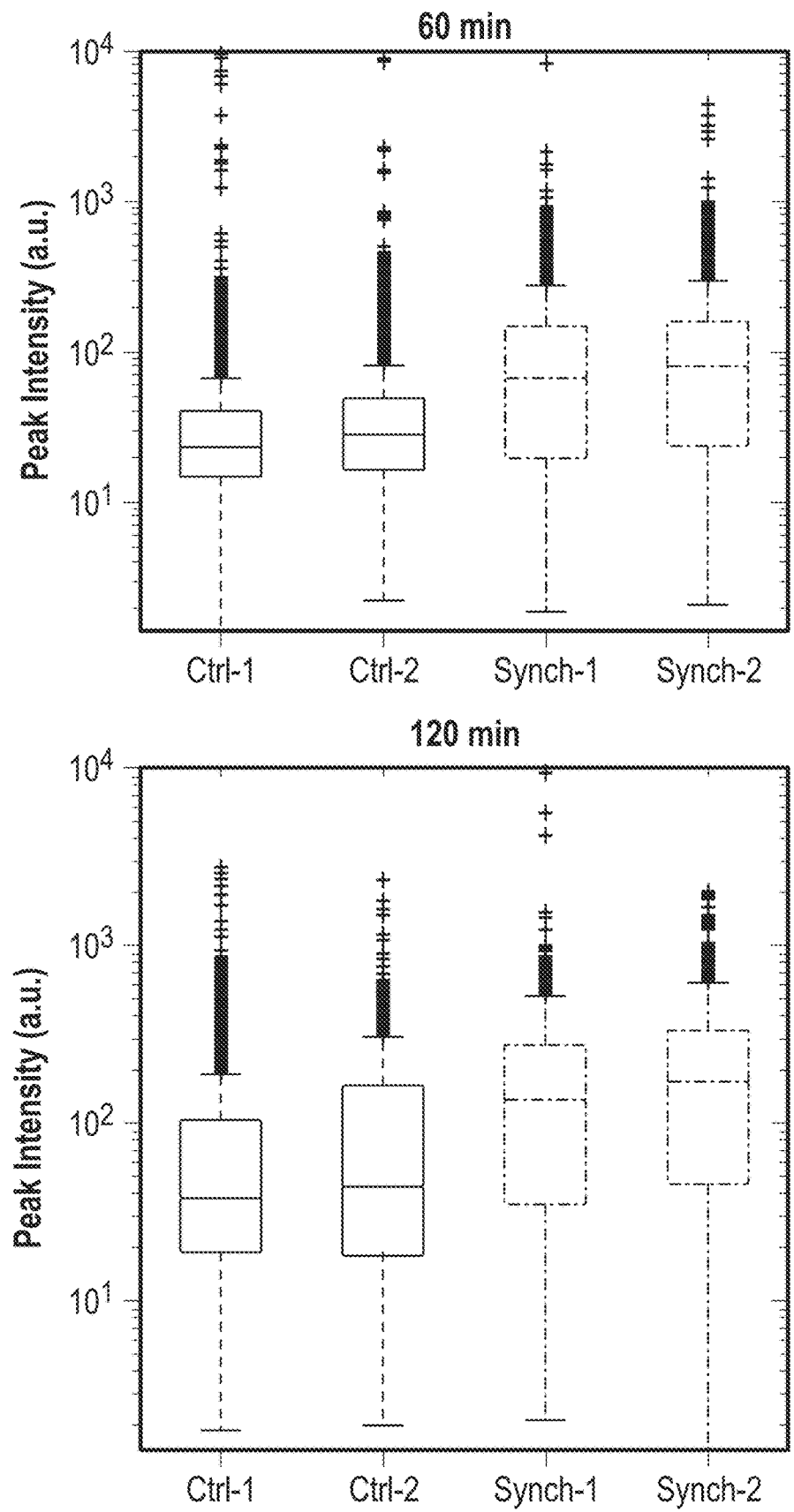
FIGS. 4A-4B show results in exemplary methods for detecting Slc17a7.
Figure 4B:
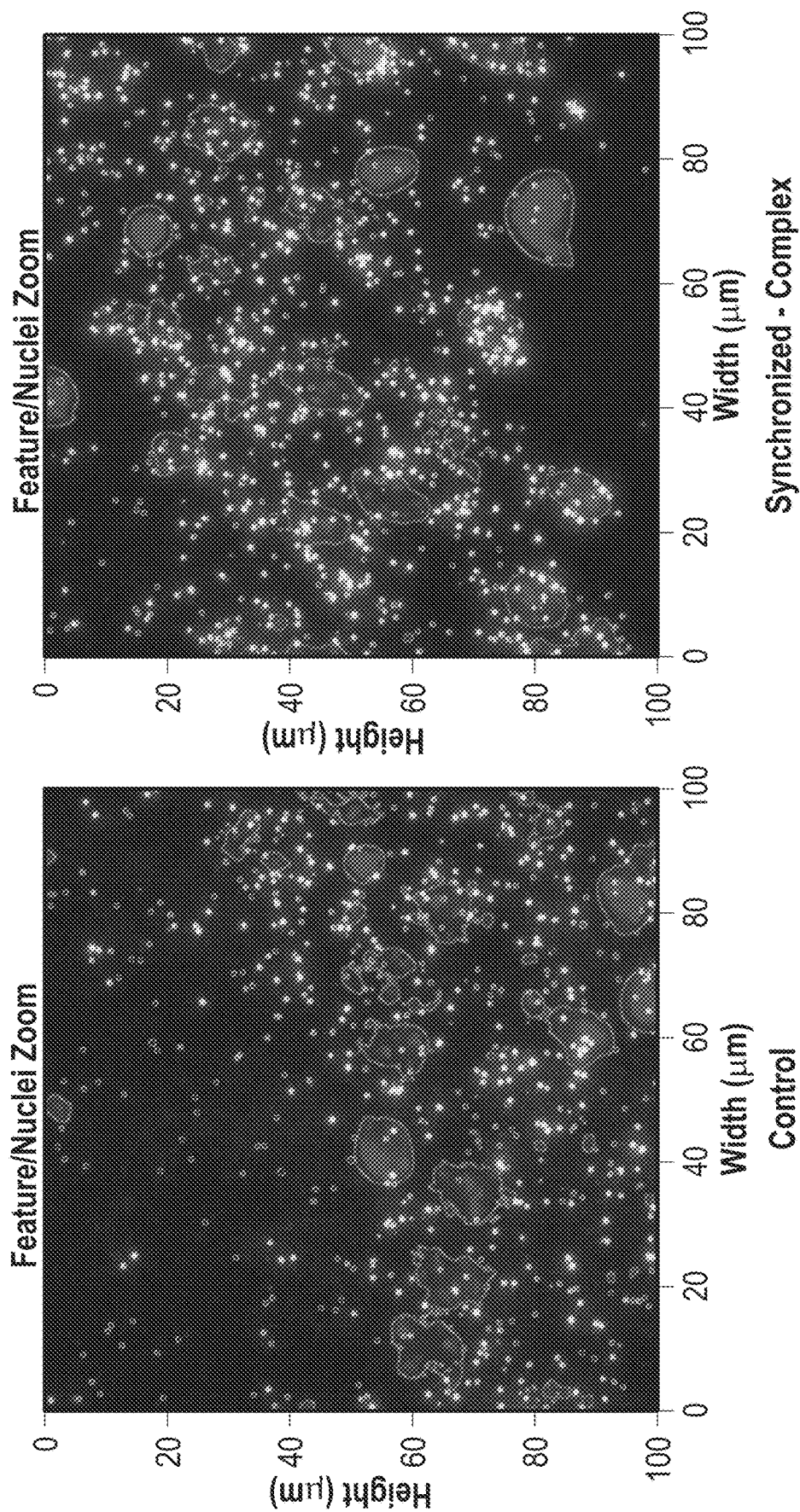

FIG. 4A shows trends of enhanced intensity under synchronized conditions relative to the control group for 60 minutes RCA and 120 minutes RCA. These results are consistent with observations of synchronized amplification in the Gad2 and Slc17a7 studies described herein. FIG. 4B shows representative images of features detected in the control and synchronized groups after 120 minutes of amplification. The synchronized group shows a trend toward more uniformity in feature intensity as compared to the control group.

FIG. 4C shows representative images after feature detection and filtering in the control and synchronized groups with 30 minutes of RCA. The synchronized group showed a trend of better detection of RCA products at the locations where Slc17a7 expression is expected in the brain tissue.

Collectively, these results indicate that synchronizing RCA by complexing polymerase and primer prior to sample application can enhance feature intensity and reduce size heterogeneity. Relative to unsynchronized control, RCA products generated using synchronized RCA may improve feature characteristics, facilitate detection and image analysis, and overall lead to more accurate detection of analytes in situ.

The present disclosure is not intended to be limited in scope to the particular disclosed embodiments, which are provided, for example, to illustrate various aspects of the disclosure. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for analyzing a biological sample, comprising:
   (a) contacting the biological sample with a first reaction mixture, wherein:
      the biological sample comprises a circular nucleic acid comprising a hybridization region, the first reaction mixture comprises a polymerase, wherein the biological sample comprises cells or is a tissue sample, the circular nucleic acid or the polymerase is prebound to a polynucleotide comprising a sequence complementary to the hybridization region, and the polymerase activity of the polymerase is inhibited; and (b) contacting the biological sample with a second reaction mixture to allow the polymerase to extend the polynucleotide hybridized to the hybridization region using the circular nucleic acid as a template, wherein a rolling circle amplification product of the circular nucleic acid is generated in the biological sample.

2. The method of claim 1, wherein the first reaction mixture is substantially free of deoxynucleoside triphosphates (dNTPs) and/or nucleoside triphosphates (NTPs).

3. The method of claim 1, wherein the first reaction mixture comprises a non-catalytic cofactor of the polymerase, wherein the non-catalytic cofactor is selected from the group consisting of: calcium, barium, strontium, iron, cobalt, nickel, tin, zinc, and europium.

4. The method of claim 1, wherein the first reaction mixture is substantially free of a catalytic cofactor of the polymerase, wherein the catalytic cofactor comprises $Mg^{2+}$, $Co^{2+}$, and/or $Mn^{2+}$.

5. The method of claim 4, wherein the first reaction mixture comprises a chelating agent, wherein the chelating agent comprises EDTA, EGTA, BAPTA, DTPA, or a combination thereof.

6. The method of claim 1, wherein the polynucleotide comprises a 3' protective group, thereby protecting the polynucleotide from 3'→5' exonuclease degradation by the polymerase while allowing priming by the polymerase.

7. The method of claim 1, wherein the polynucleotide is a primer, and the primer is prebound to the polymerase in the first reaction mixture prior to contacting the biological sample in step (a).

8. The method of claim 1, wherein the polynucleotide is a primer, and the primer is prebound to the circular nucleic acid in the biological sample prior to contacting the first reaction mixture in step (a).

9. The method of claim 8, wherein the hybridization region in the circular nucleic acid is a primer hybridization region that hybridizes to the primer, and the circular nucleic acid further comprises a target hybridization region that hybridizes to a target nucleic acid.

10. The method of claim 1, wherein the polynucleotide is a target nucleic acid, and the target nucleic acid is prebound to the circular nucleic acid in the biological sample prior to and/or during contacting the first reaction mixture in step (a).

11. The method of claim 1, wherein the second reaction mixture:
(a) comprises a deoxynucleoside triphosphate (dNTP) and/or a nucleoside triphosphate (NTP);
(b) comprises a catalytic cofactor of the polymerase, wherein the catalytic cofactor is a di-cation; and
(c) is substantially free of the polymerase and/or other polymerases.

12. The method of claim 1, wherein the polynucleotide hybridized to the hybridization region is extended by the polymerase using the circular nucleic acid as a template, thereby generating the rolling circle amplification product.

13. The method of claim 1, wherein the method comprises imaging the biological sample to detect the rolling circle amplification product.

14. The method of claim 13, wherein the imaging comprises detecting a signal associated with a fluorescently labeled probe that directly or indirectly binds to the rolling circle amplification product.

15. The method of claim 1, wherein a sequence of the rolling circle amplification product is analyzed in situ in the biological sample.

16. The method of claim 1, wherein:
the circular nucleic acid is formed in the biological sample from a probe or a probe set for a target molecule,
the target molecule is genomic DNA, mitochondrial DNA, mRNA or cDNA, and
the probe or probe set for the target molecule comprises a padlock probe that hybridizes to the genomic DNA, mitochondrial DNA, mRNA or cDNA.

17. The method of claim 1, wherein the first reaction mixture comprises a non-catalytic metal ion.

18. The method of claim 17, wherein the non-catalytic metal ion is $Ca^{2+}$ or $Sr^{2+}$.

19. The method of claim 1, wherein the polymerase is selected from the group consisting of Phi29 DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, Klenow fragment, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof.

20. The method of claim 1, further comprising, between the contacting in step (a) and step (b), a step of removing molecules of the polymerase and/or the polynucleotide that are not bound to the circular nucleic acid from the biological sample.

* * * * *